US009622645B2

(12) United States Patent
Moriya

(10) Patent No.: US 9,622,645 B2
(45) Date of Patent: Apr. 18, 2017

(54) MEDICAL IMAGE PROCESSING DEVICE AND METHOD FOR OPERATING THE SAME

(71) Applicant: FUJIFILM Corporation, Tokyo (JP)

(72) Inventor: Yoshiyuki Moriya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 115 days.

(21) Appl. No.: 14/665,784

(22) Filed: Mar. 23, 2015

(65) Prior Publication Data

US 2015/0269741 A1  Sep. 24, 2015

(30) Foreign Application Priority Data

Mar. 24, 2014 (JP) ................ 2014-060173
Jun. 27, 2014 (JP) ................ 2014-133392

(51) Int. Cl.
*G06K 9/34* (2006.01)
*A61B 1/00* (2006.01)
*H04N 1/62* (2006.01)
*G06T 7/00* (2017.01)
*G06T 7/90* (2017.01)

(52) U.S. Cl.
CPC ........ *A61B 1/00009* (2013.01); *G06T 7/0012* (2013.01); *G06T 7/90* (2017.01); *H04N 1/622* (2013.01); *A61B 1/00* (2013.01); *G06T 2207/10068* (2013.01); *G06T 2207/30096* (2013.01); *G06T 2207/30101* (2013.01)

(58) Field of Classification Search
CPC ..... A61B 1/00; A61B 1/00009; G06T 7/0012; G06T 7/408; G06T 2207/10068; G06T 2207/30096; G06T 2207/30101; H04N 1/622

USPC .......... 382/164; 600/109, 323; 345/589, 89, 345/591
See application file for complete search history.

(56) References Cited

U.S. PATENT DOCUMENTS 4,860,091 A   8/1989   Kimura et al.
5,515,449 A   5/1996   Tsuruoka et al.
(Continued)

FOREIGN PATENT DOCUMENTS

EP   1618828 A1   1/2006
JP   3228627 B2   11/2001
(Continued)

OTHER PUBLICATIONS

Extended European Search Report dated Sep. 8, 2015, for European Application No. 15160179.6.

*Primary Examiner* — Mekonen Bekele
(74) *Attorney, Agent, or Firm* — Birch, Stewart, Kolasch & Birch, LLP

(57) ABSTRACT

RGB image signals are inputted. B/G ratio is calculated based on B image signal and G image signal. G/R ratio is calculated based on the G image signal and R image signal. In a feature space formed by the B/G ratio and the G/R ratio, an expansion process and a compression process are performed. In the expansion process, an angle between a first center line and coordinates in a specific region, which contains the first center line, is changed at an angle change rate Wnx. In the compression process, an angle between the first center line and coordinates outside the specific region is changed at an angle change rate Wny smaller than the angle change rate Wnx.

11 Claims, 26 Drawing Sheets

(56) References Cited

U.S. PATENT DOCUMENTS

| | | | | |
|---|---|---|---|---|
| 2002/0122020 A1* | 9/2002 | Moon | ............... | G09G 3/3406 |
| | | | | 345/89 |
| 2009/0027413 A1* | 1/2009 | Pyo | ............... | G09G 5/02 |
| | | | | 345/589 |
| 2012/0116192 A1* | 5/2012 | Saito | ............... | A61B 1/00009 |
| | | | | 600/323 |
| 2012/0197077 A1* | 8/2012 | Kaku | ............... | A61B 1/00009 |
| | | | | 600/109 |
| 2012/0253122 A1* | 10/2012 | Minetoma | ............... | A61B 1/00057 |
| | | | | 600/109 |
| 2014/0333655 A1* | 11/2014 | Tu | ............... | G09G 5/02 |
| | | | | 345/591 |
| 2015/0269750 A1* | 9/2015 | Moriya | ............... | G06T 7/408 |
| | | | | 382/128 |

FOREIGN PATENT DOCUMENTS

| | | |
|---|---|---|
| WO | WO 2014/156937 A1 | 10/2014 |
| WO | WO 2014/156938 A1 | 10/2014 |

\* cited by examiner (A)  FIRST PROCESS  (B)

MEDICAL IMAGE PROCESSING DEVICE AND METHOD FOR OPERATING THE SAME

CROSS-REFERENCE TO RELATED APPLICATIONS

The present application claims priority under 35 U.S.C. §119 to Japanese Patent Application No. 2014-060173, filed Mar. 24, 2014 and Japanese Patent Application No. 2014-133392, filed Jun. 27, 2014. The above application is hereby expressly incorporated by reference, in its entirety, into the present application.

BACKGROUND OF THE INVENTION

1. Field of the Invention

The present invention relates to a medical image processing device for taking and displaying a medical image of an object of interest in a body cavity and a method for operating a medical image processing device.

2. Description Related to the Prior Art

In medical fields, diagnoses using endoscope systems have been commonly performed. The endoscope system comprises a light source device, an endoscope, and a processor device. In the endoscope system, an image of the object is displayed on a monitor based on the image signal. The image signal is obtained by taking an image of an object of interest (hereinafter simply referred to as the object), with an image sensor of the endoscope, under illumination light from the endoscope. A doctor examines presence or absence of a lesion while observing the image displayed on the monitor.

It is easy to detect a lesion which differs significantly in shape and size from a normal region, for example, a lesion protruding sharply from a mucosal surface. On the other hand, a lesion which is almost the same in shape and size as the normal region is detected based on a difference in color from that of the normal region. It is extremely difficult to detect a lesion in a case where the lesion has not progressed and the color thereof is almost the same as that of the normal region.

In Japanese Patent No. 3228627, a difference in color between a normal region and a lesion is made distinct or apparent by replacing a value of a blood volume (hemoglobin index) of the lesion, which is deviated from a reference value, with a more deviated value.

In the case where the value deviated from the reference value is replaced with the more deviated value as described in the Japanese Patent No. 3228627, not only a color in a specific color region where the color is to be enhanced but also a color outside the specific color region may be changed. The image with the color outside the specific color region being changed may cause a doctor to fail to diagnose accurately.

SUMMARY OF THE INVENTION

An object of the present invention is to provide a medical image processing device for producing an image in which a color in a specific color region is changed while a color outside the specific color region is not changed and a method for operating a medical image processing device.

The medical image processing device comprises an input processing unit, a color information obtaining section, and a processor. The input processing unit performs an input process of a first color image signal. The color information obtaining section obtains two or more pieces of color information from the first color image signal. The processor performs an expansion process for changing an angle between a center line and coordinates within a specific angle changing region Rnx containing the center line at an angle change rate Wnx and a compression process for changing an angle between the center line and coordinates within an angle changing region Rny beyond the angle changing region Rnx at an angle change rate Wny in a feature space. The feature space is formed by the two or more pieces of color information. The angle change rate Wny is less than the angle change rate Wnx.

It is preferred that first and second observation areas to be observed are distributed in the feature space, and a distance between the first observation area and the second observation area is D1. The center line is a first center line provided between the first observation area and the second observation area. The angle changing region Rnx is an angle changing region R1x containing the first center line. The angle changing region Rny is an angle changing region R1y beyond the angle changing region R1x. The angle change rate Wnx is an angle change rate W1x greater than 1. The angle change rate Wny is an angle change rate W1y less than 1.

It is preferred that the first observation area, the second observation area, and a third observation area are distributed in the feature space. A distance D2 between the first observation area and the third observation area is greater than the distance D1. The center line is a second center line provided between the first observation area and the third observation area. The angle changing region Rnx is an angle changing region R2x containing the second center line. The angle changing region Rny is an angle changing region R2y beyond the angle changing region R2x. The angle change rate Wnx is an angle change rate W2x greater than 1. The angle change rate Wny is an angle change rate W2y less than 1.

It is preferred that the angle after the expansion process or the compression process is within a region extending between ±90° from the first or second center line.

It is preferred that fourth and fifth observation areas to be observed are distributed in the feature space. The center line is a third center line provided between the fourth observation area and the fifth observation area. The angle changing region Rnx is a specific angle changing region R3x located on a fourth observation area side from the third center line. The angle changing region Rny is an angle changing region R3y beyond the angle changing region R3x. The angle change rate Wnx is an angle change rate W3x greater than 1. The angle change rate Wny is an angle change rate W3y less than 1.

It is preferred that the first color image signal is composed of image signals of three colors. The two or more pieces of color information is composed of a first signal ratio between the image signals of the two colors of out of the image signals of the three colors and a second signal ratio between the image signals of the two colors out of the image signals of the three colors. One of the colors of the image signals of the second signal ratio differs from the colors of the image signals of the first signal ratio. The feature space is a signal ratio space formed by the first and second signal ratios.

It is preferred that the first signal ratio correlates with a blood vessel depth and the second signal ratio correlates with a blood volume. It is preferred that the first signal ratio is a B/G ratio and the second signal ratio is a G/R ratio.

It is preferred that the feature space is any one of a CbCr space formed by chrominance signals Cr and Cb, being the two or more pieces of color information, or an ab space formed by color components a* and b*, being the two or more pieces of color information, in a CIE-Lab space.

It is preferred that the medical image processing device further comprises a color image signal converter and a brightness adjuster. The color image signal converter converts the two or more pieces of color information, which have been subjected to the processes in the processor, into a second color image signal. The brightness adjuster adjusts a pixel value of the second color image signal based on first brightness information obtained from the first color image signal and second brightness information obtained from the second color image signal.

The method for operating a medical image processing device comprises an input process step, a color information obtaining step, and an expansion and compression step. In the input process step, the input processing unit performs an input process of a first color image signal. In the color information obtaining step, a color information obtaining section obtains two or more pieces of color information from the first color image signal. In the expansion and compression step, a processor performs an expansion process for changing an angle between a center line and coordinates within a specific angle changing region Rnx containing the center line at an angle change rate Wnx and a compression process for changing an angle between the center line and coordinates within an angle changing region Rny beyond the angle changing region Rnx at an angle change rate Wny in a feature space. The feature space is formed by the two or more pieces of color information. The angle change rate Wny is less than the angle change rate Wnx.

According to the present invention, the medical image processing device produces an image in which a color in a specific color region is changed while a color outside the specific color region is not changed.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS (First Embodiment)

Figure 1:
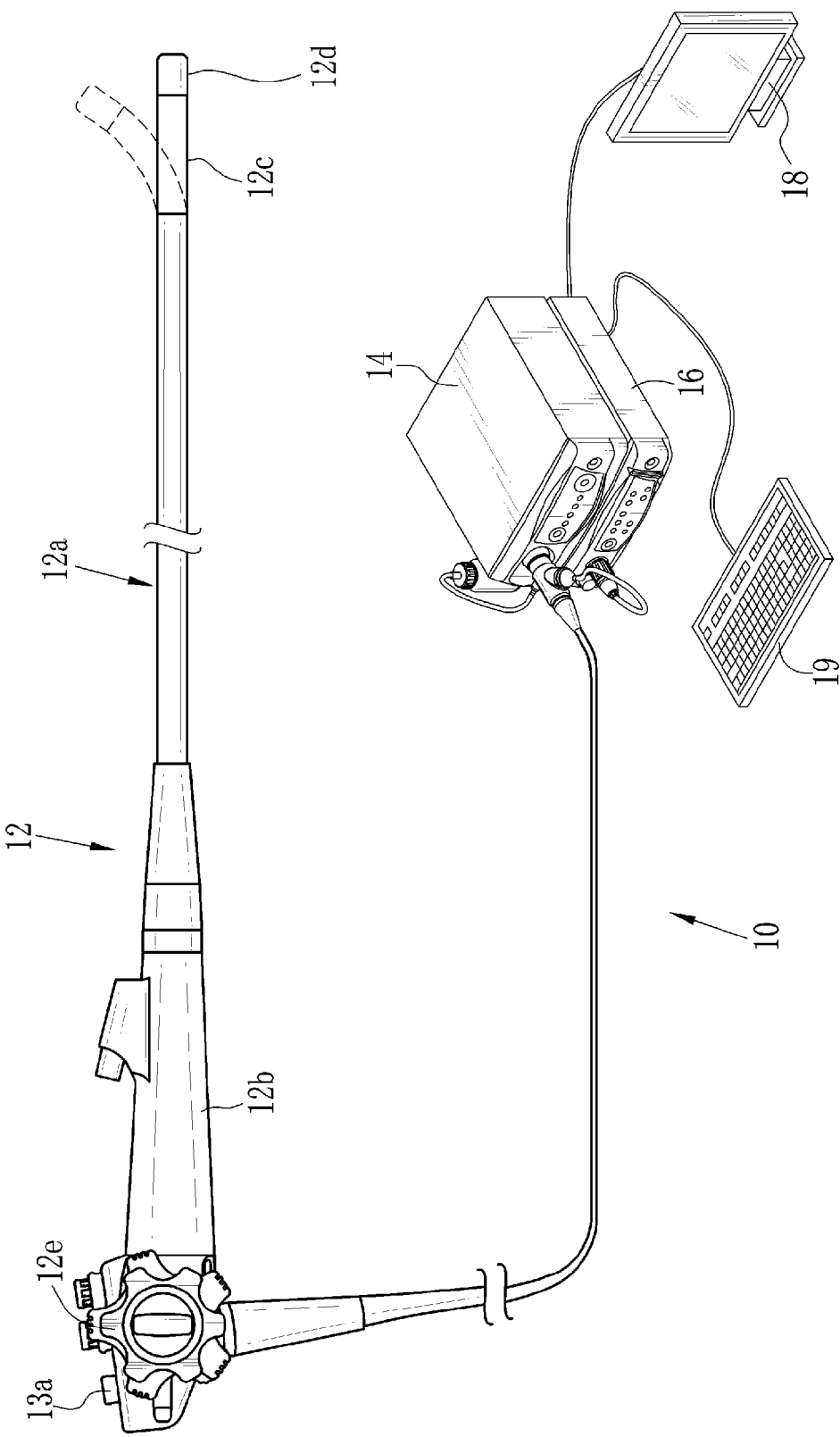
FIG. 1 is an external view of an endoscope system according to a first embodiment.

As illustrated in FIG. 1, an endoscope system 10 of a first embodiment comprises an endoscope 12, a light source device 14, a processor device 16, a monitor 18, and a console 19. The endoscope 12 is connected optically to the light source device 14, and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e and a mode switch (SW) 13a. The mode SW 13a is operated to switch among three modes: a normal mode, a first special mode, and a second special mode. In the normal mode, a normal image of an object of interest (hereinafter simply referred to as the object) is displayed on the monitor 18. The first special mode is used to determine whether the eradication (removal) of *Helicobacter pylori* (*H. pylori*) infection has been successful. In the first special mode, a first special image is displayed on the monitor 18. The second special mode is used to detect or determine the *H. pylori* infection. In the second special mode, a second special image is displayed on the monitor 18.

The processor device 16 is electrically connected to the monitor 18 and the console 19. The monitor 18 outputs and displays image information and the like. The console 19 functions as a UI (user interface), which receives input operation such as setting a function. Note that an external storage unit (not shown) for recording the image information and the like may be connected to the processor device 16.

Figure 2:
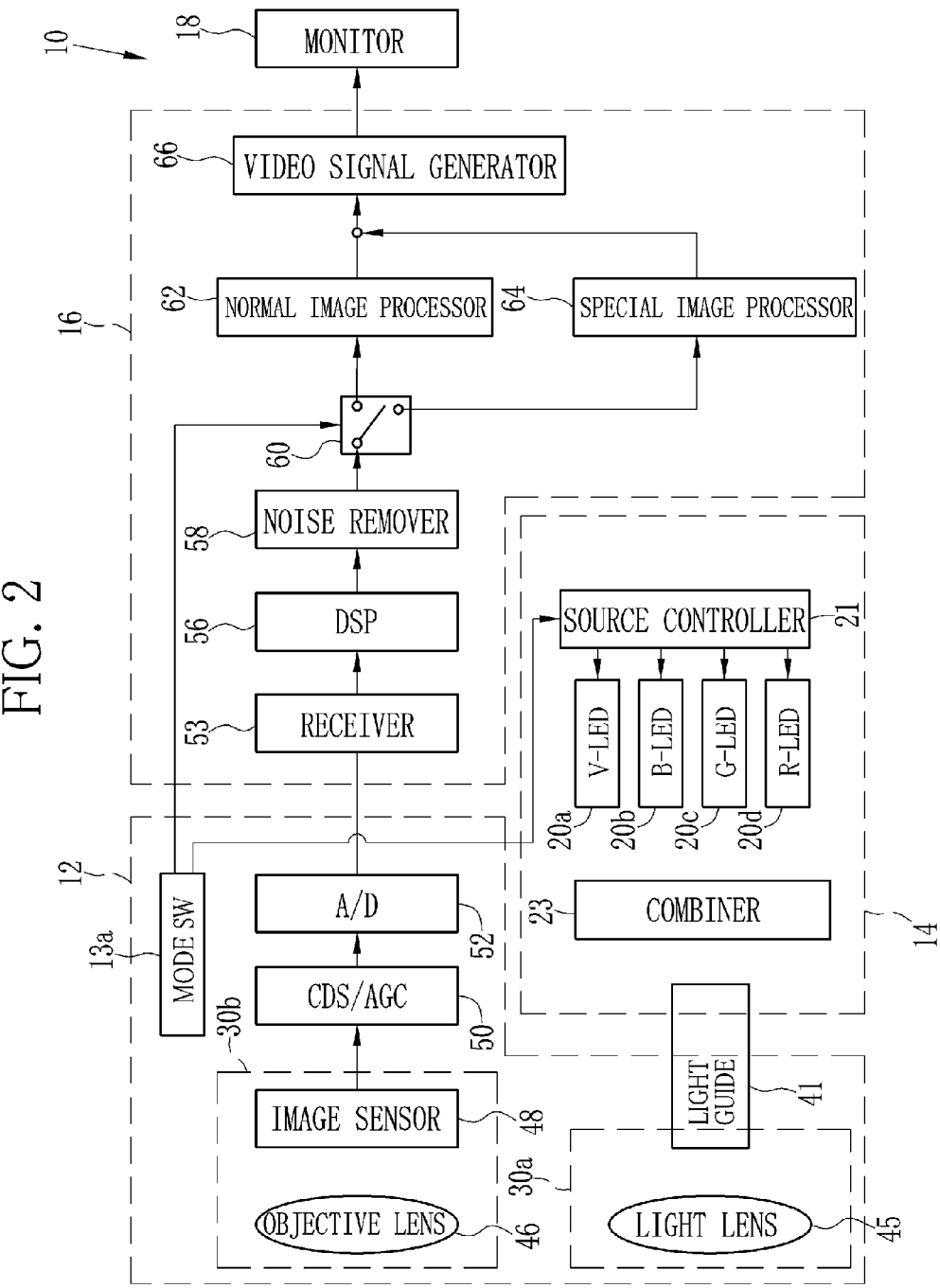
FIG. 2 is a block diagram illustrating the endoscope system according to the first embodiment.

As illustrated in FIG. 2, the light source device 14 comprises a V-LED (Violet Light Emitting Diode) 20a, a B-LED (Blue Light Emitting Diode) 20b, a G-LED (Green Light Emitting Diode) 20c, an R-LED (Red Light Emitting Diode) 20d, a source controller 21 for controlling the LEDs 20a to 20d, and a combiner 23. The combiner 23 combines the optical paths of four colors of light from the four colors of the LEDs 20a to 20d together. The light combined by the combiner 23 is applied to the object in a body cavity through a light guide (LG) 41 and a light lens 45. The light guide 41 extends inside the insertion section 12a. Note that an LD (Laser Diode) may be used in place of the LED.

Figure 3:
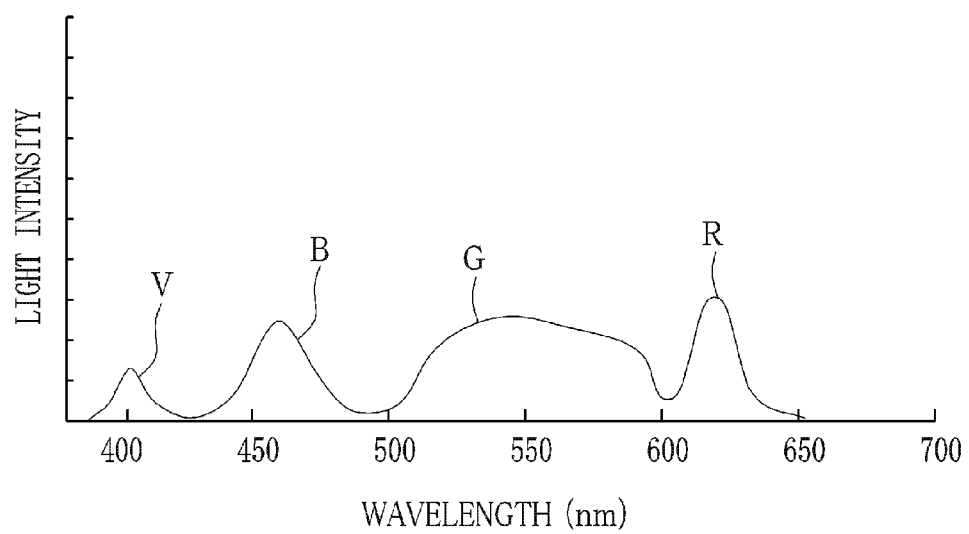
FIG. 3 is a graph illustrating an emission spectra of violet light V, blue light B, green light G, and red light R.

As illustrated in FIG. 3, the V-LED 20a generates violet light V having a wavelength range 380-420 nm and the center wavelength 405±10 nm. The B-LED 20b generates blue light B having a wavelength range 420-500 nm and the center wavelength 460±10 nm. The G-LED 20c generates green light G having a wavelength range 480-600 nm. The R-LED 20d generates red light R having a wavelength range 600-650 nm and the center wavelength 620-630 nm. In each of the LEDs 20a to 20d, note that the center wavelength may be the same as or different from the peak wavelength.

In each of the normal mode, the first special mode, and the second special mode, the source controller 21 turns on the V-LED 20a, the B-LED 20b, the G-LED 20c, and the R-LED 20d. In other words, the mixture of the violet light V, the blue light B, the green light G, and the red light R is applied to the object. In the normal mode, the source controller 21 controls the LEDs 20a to 20d to make a light quantity ratio among the violet light V, the blue light B, the green light G, and the red light R to be Vc:Bc:Gc:Rc. In the first and second special modes, the source controller 21 controls the LEDs 20a to 20d to make the light quantity ratio among the violet light V, the blue light B, the green light G, and the red light R to be Vs:Bs:Gs:Rs.

As illustrated in FIG. 2, the light guide 41 extends inside the endoscope 12 and a universal cord that connects the endoscope 12, the light source device 14, and the processor device 16. The light guide 41 transmits the light combined by the combiner 23 to the distal portion 12d of the endoscope 12. Note that a multimode fiber is used as the light guide 41. For example, a small-diameter fiber cable with the core diameter 105 μm, the clad diameter 125 μm, and the outer diameter ϕ 0.3 to 0.5 mm (including a protection layer, being a jacket) may be used.

The distal portion 12d of the endoscope 12 comprises an illumination optical system 30a and an imaging optical system 30b. The illumination optical system 30a has the light lens 45. The light from the light guide 41 is applied to the object through the light lens 45. The imaging optical system 30b has an objective lens 46 and an image sensor 48. The reflection light from the object is incident on the image sensor 48 through the objective lens 46. Thereby a reflection image of the object is formed on the image sensor 48.

The image sensor 48 is a color image sensor. The image sensor 48 captures the reflection image of the object, and outputs an image signal. It is preferred that the image sensor 48 is a CCD (Charge Coupled Device) image sensor, a CMOS (Complementary Metal-Oxide Semiconductor) image sensor, or the like. The image sensor 48 used in the present invention is a color image sensor for obtaining image signals of three colors, R (red), G (green), and B (blue), that is, a so-called RGB image sensor comprising R pixels with R filters, G pixels with G filters, and B pixels with B filters.

Note that the image sensor 48 may be a so-called complementary color image sensor instead of the RGB image sensor. The complementary color image sensor has complementary color filters of C (cyan), M (magenta), Y (yellow), and G (green). In the case where the complementary color image sensor is used, four colors (CMYG) of image signals are outputted. It is necessary to convert the four colors (CMYG) of image signals into three colors (RGB) of image signals through complementary color/primary color conversion. Alternatively, the image sensor 48 may be a monochrome image sensor with no color filters. In this case, it is necessary that the source controller 21 applies the blue light B, the green light G, and the red light R in a time-division manner. It is also necessary to synchronize the processing of the image signals.

The image signal outputted from the image sensor 48 is transmitted to a CDS/AGC circuit 50. The CDS/AGC circuit 50 performs correlated double sampling (CDS) and automatic gain control (AGC) on the image signal, being an analog signal. The image signal which has passed through the CDS/AGC circuit 50 is converted into a digital image signal by an A/D converter 52. The A/D converted digital image signal is inputted to the processor device 16.

The processor device 16 comprises a receiver 53, a DSP (Digital Signal Processor) 56, a noise remover 58, an image processing selector 60, a normal image processor 62, a special image processor 64, and a video signal generator 66. The receiver 53 receives the digital RGB image signals from the endoscope 12. The R image signal corresponds to (or refers to) signals outputted from the R pixels of the image sensor 48. The G image signal corresponds to (or refers to) signals outputted from the G pixels of the image sensor 48. The B image signal corresponds to (or refers to) signals outputted from the B pixels of the image sensor 48.

The DSP 56 performs various types of signal processing (defect correction process, offset processing, gain correction process, linear matrix processing, gamma conversion process, demosaicing process, and the like) on the image signal received. In the defect correction process, signals from defective pixels in the image sensor 48 are corrected. In the offset processing, dark current components are removed from the RGB image signals which have been subjected to the defect correction process. Thereby an accurate zero level is set. In the gain correction process, a signal level is adjusted or corrected by multiplying a specific gain to the RGB image signals after the offset processing. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process) in which color signal(s) lacking in each pixel is generated by interpolation. Owing to the demosaicing process, each pixel has three colors (RGB) of signals.

The DSP 56 performs gamma correction and the like on the RGB image signals. Thereafter, the noise remover 58 removes noise from the RGB image signals through a noise removing process (for example, moving average method or median filter method). Then, the RGB image signals are transmitted to the image processing selector 60. Note that "input processing unit" of the present invention corresponds to the configuration comprising the receiver 53, the DSP 56, and the noise remover 58.

In the normal mode, which is set using the mode SW 13a, the image processing selector 60 transmits the RGB image signals to the normal image processor 62. In the case where the mode is set to the first special mode or the second special mode, the image processing selector 60 transmits the RGB image signals to the special image processor 64.

The normal image processor 62 performs color conversion process, color enhancement process, and structure enhancement process on the RGB image signals. In the color conversion process, the digital RGB image signals are subjected to 3×3 matrix processing, tone conversion process, three-dimensional LUT process, and the like. Thereby the digital RGB image signals are converted into the color-converted RGB image signals. Next, the color-converted RGB image signals are subjected to various types of color enhancement processes. The color-enhanced RGB image signals are subjected to the structure enhancement process (e.g. spatial frequency enhancement and the like). The structure-enhanced RGB image signals are inputted as the RGB image signals of the normal image from the normal image processor 62 to the video signal generator 66.

The special image processor 64 produces the first special image and the second special image based on the RGB image signals. In the first special image, a difference in color of the object between a portion infected with the *H. pylori* and a portion in which the *H. pylori* infection has been eradicated successfully is enhanced. In the second special image, a difference in color of the object between the portion infected with the *H. pylori* and a portion uninfected with the *H. pylori* is enhanced. The special image processor 64 will be described in detail below. The RGB image signals of the first or second special image, which is produced by the special image processor 64, are inputted to the video signal generator 66.

The video signal generator 66 converts the RGB image signals, which are inputted from the normal image processor 62 or the special image processor 64, into a video signal to be displayed as an image on the monitor 18. The monitor 18 displays the normal image, the first special image, or the second special image based on the video signal.

Figure 4:
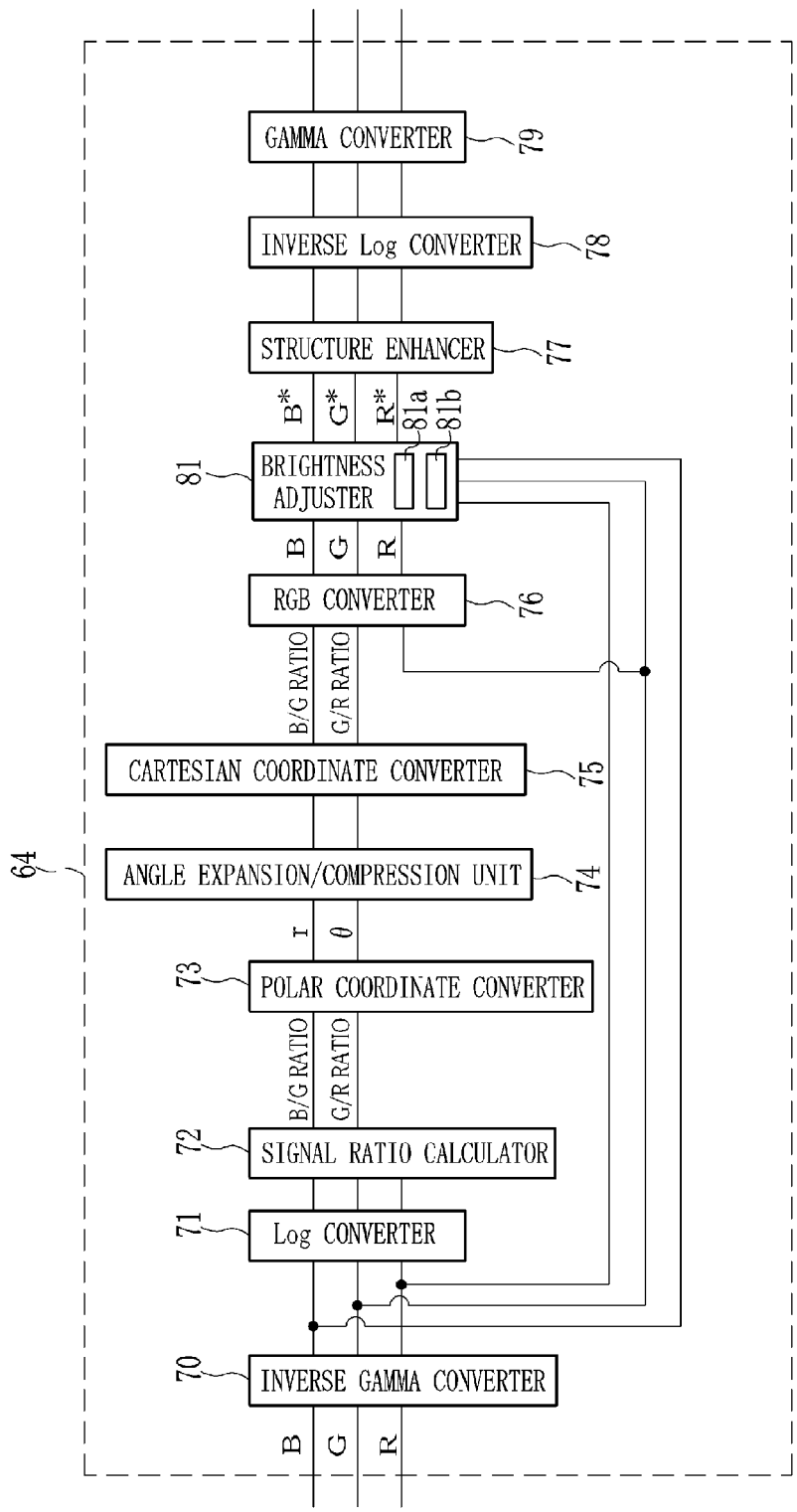
FIG. 4 is a block diagram illustrating functions of a special image processor.

As illustrated in FIG. 4, the special image processor 64 comprises an inverse gamma converter 70, a log converter 71, a signal ratio calculator 72, a polar coordinate converter 73, an angle expansion/compression unit (processor) 74, a Cartesian coordinate converter 75, an RGB converter 76, a structure enhancer 77, an inverse log converter 78, and a gamma converter 79. The special image processor 64 also comprises a brightness adjuster 81 between the RGB converter 76 and the structure enhancer 77.

The inverse gamma converter 70 performs inverse gamma conversion on the inputted digital image signal of the RGB channels. The RGB image signals after the inverse gamma conversion are linearly-changing RGB signals which change linearly relative to reflectance from the object. Owing to this, a proportion of the signal components related to various types of biological information increases in the RGB image signals. Note that the linearly-changing R image signal is referred to as a first R image signal. The linearly-changing G image signal is referred to as a first G image signal. The linearly-changing B image signal is referred to as a first B image signal.

The log converter 71 performs log conversion of each of the linearly-changing RGB image signals (which correspond to "first color image signal" of the present invention). Thereby, log-converted R image signal (log R), log-converted G image signal (log G), and log-converted B image signal (log B) are obtained. The signal ratio calculator 72 (which corresponds to a "color information obtaining section" of the present invention) performs difference processing (log G-log B=log G/B=−log (B/G)) based on the log-converted G image signal and the log-converted B image signal. Thereby, the B/G ratio is calculated. The B/G ratio refers to −log(B/G) with the "−log" omitted. The G/R ratio is calculated by difference processing (log R-log G=log R/G=−log(G/R)) based on the log-converted R image signal and the log-converted G image signal. The G/R ratio refers to −log (G/R) with the "−log" omitted in a manner similar to the B/G ratio.

Note that the B/G ratio and the G/R ratio are calculated with respect to the pixels in the same positions in the B image signal, the G image signal, and the R image signal. The B/G ratio and the G/R ratio are calculated for each pixel. The B/G ratio correlates with a blood vessel depth (distance between the mucosal surface and a position of a specific blood vessel), so that the B/G ratio varies with the blood vessel depth. The G/R ratio correlates with the blood volume (hemoglobin index), so that the G/R ratio varies with the blood volume.

The polar coordinate converter 73 converts the B/G ratio and the G/R ratio, which are calculated by the signal ratio calculator 72, into a radial coordinate r and an angular coordinate θ. The polar coordinate converter 73 performs the conversion into the radial coordinate r and the angular coordinate θ for each pixel. In the first special mode, the angle expansion/compression unit 74 performs a first process. The first process refers to increasing the difference between a first observation area and a second observation area. In the first observation area, the radial coordinates r and the angular coordinates θ corresponding to a portion (of the object) infected with the *H. pylori* are distributed. In the second observation area, the radial coordinates r and the angular coordinates θ corresponding to a portion (of the object) in which the eradication of the *H. pylori* infection has been successful are distributed. In the second special mode, the angle expansion/compression unit 74 performs a second process. The second process refers to increasing the difference between the first observation area and a third observation area. In the first observation area, the radial coordinates r and the angular coordinates θ corresponding to a portion (of the object) infected with the *H. pylori* are distributed. In the third observation area, the radial coordinates r and the angular coordinates θ corresponding to a portion (of the object) uninfected with the *H. pylori* are distributed. The first and second processes will be described in details below.

The Cartesian coordinate converter 75 converts the angle-expanded or angle-compressed radial coordinate r and angular coordinate θ, which have passed through the angle expansion/compression unit 74, into Cartesian coordinates. Thereby the angle-expanded or angle-compressed B/G and G/R ratios are obtained. The RGB converter 76 (which corresponds to a "color image signal converter" of the present invention) uses at least one of the first RGB image signals to convert the angle-expanded or angle-compressed B/G and G/R ratios into the RGB image signals. To convert the B/G ratio into a second B image signal, the RGB converter 76 performs arithmetic operations based on the B/G ratio and the G image signal of the first RGB image signals, for example. To convert the G/R ratio into a second R image signal, the RGB converter 76 performs arithmetic operations based on the G/R ratio and the G image signal of the first RGB image signals, for example. The RGB converter 76 outputs the first G image signal as a second G image signal, without any conversion.

The brightness adjuster 81 adjusts or corrects the pixel values of the second RGB image signals based on the first RGB image signals and the second RGB image signals. A reason for adjusting the pixel values of the second RGB image signals by the brightness adjuster 81 is as follows. Brightness of the second RGB image signals, which are obtained by the expansion and compression processes in the color region by the angle expansion/compression unit 74, may become significantly different from brightness of the first RGB image signals. The brightness adjuster 81 adjusts the pixel values of the second RGB image signals to make the brightness of the second RGB image signals after the brightness adjustment equal to the brightness of the first RGB image signals.

The brightness adjuster 81 comprises a first brightness information calculator 81a and a second brightness information calculator 81b. The first brightness information calculator 81a calculates first brightness information Yin based on the first RGB image signals. The second brightness information calculator 81b calculates second brightness information Yout based on the second RGB image signals. The first brightness information calculator 81a calculates the first brightness information Yin with the use of an arithmetic expression "kr×pixel value of first R image signal+kg×pixel value of first G image signal+kb×pixel value of first B image signal". The second brightness information calculator 81b calculates the second brightness information Yout in a manner similar to that of the first brightness information calculator 81a, with the use of an arithmetic expression similar to that described above. After calculating the first brightness information Yin and the second brightness information Yout, the brightness adjuster 81 performs arithmetic operations based on the expressions (E1) to (E3), thereby adjusting the pixel values of the second RGB image signals.

$$R^* = \text{pixel value of second } R \text{ image signal} \times Yin/Yout \quad (E1)$$

$$G^* = \text{pixel value of second } G \text{ image signal} \times Yin/Yout \quad (E2)$$

$$B^* = \text{pixel value of second } B \text{ image signal} \times Yin/Yout \quad (E3)$$

Note that "R*" denotes the second R image signal after the brightness adjustment. "G*" denotes the second G image signal after the brightness adjustment. "B*" denotes the second B image signal after the brightness adjustment. Each of "kr", "kg", and "kb" is an arbitrary constant within a range from 0 to 1.

The structure enhancer 77 performs the structure enhancement process (e.g. frequency filtering or the like) on the second RGB image signals which have passed through the RGB converter 76. The inverse log converter 78 performs inverse log conversion on the second RGB image signals which have passed through the structure enhancer 77. Thereby the second RGB image signals with antilogarithmic pixel values are obtained. The gamma converter 79 performs the gamma conversion on the RGB image signals which have passed through the inverse log converter 78. Thereby the second RGB image signals with the tone suitable for an output device such as the monitor 18 are obtained. The RGB image signals, which have passed through the gamma converter 79, are transmitted as the RGB image signals of the first or second special image to the video signal generator 66.

Figure 5:
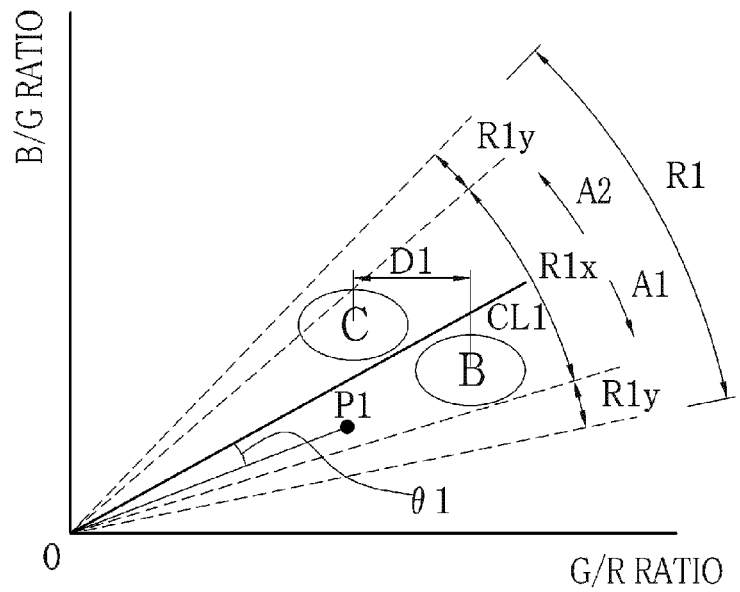
FIG. 5 is an explanatory view illustrating a first process.

The first and second processes performed by the angle expansion/compression unit 74 are described using a feature space (hereinafter referred to as the signal ratio space), being a two-dimensional space formed by the B/G ratio (vertical axis) and the G/R ratio (horizontal axis) as illustrated in FIG. 5. In the first process (for the signal ratio space), a region including the first observation area (denoted as "B" in FIG. 5 and so forth) and the second observation area (denoted as "C" in FIG. 5 and so forth) is set as an angle changing region R1 in the signal ratio space. In the first observation area, the coordinates corresponding to a portion infected with the *H. pylori* are distributed. In the second observation area, the coordinates corresponding to a portion in which the eradication of the *H. pylori* infection has been successful are distributed. Then, the angles θ of the coordinates in the angle changing region R1 are changed while the angles θ of the coordinates outside the angle changing region R1 are not changed. In the first process (for the signal ratio space), the radial coordinates r of the coordinates in the angle changing region R1 are not changed. Note that there is a distance D1 between the average value of the first observation area and the average value of the second observation area.

In the angle changing region R1, a first center line CL1 is set to a portion which is considered to be the boundary between the first observation area and the second observation area. Coordinates (point) P1 within the angle changing region R1 are defined by an angle "θ1" from the first center line CL1. The angle θ1 is defined as a positive value in a case where the angle θ1 is situated in the clockwise direction A1 from the first center line CL1. The angle θ1 is defined as a negative value in a case where the angle θ1 is situated in the counterclockwise direction A2 from the first center line CL1.

Figure 6:
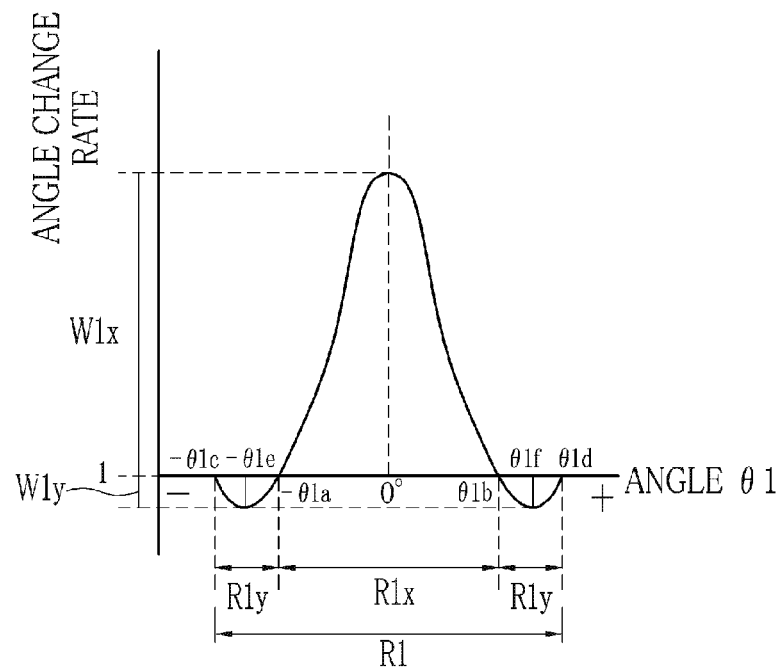
FIG. 6 is a graph illustrating a relationship between an angle θ1 and an angle change rate at the first process for a signal ratio space.

As illustrated in FIG. 6, in the first process (for the signal ratio space), the expansion process is performed on the coordinates in an angle changing region R1x, which contains the first center line CL1 and extends within the angle changing region R1. In the expansion process, the angle θ1 is changed at the angle change rate W1x greater than "1". The angle changing region R1x refers to a region between "−θ1a" to "θ1b". The compression process is performed on the coordinates in an angle changing region R1y, which is outside the angle changing region R1x, but within the angle changing region R1. In the compression process, the angle θ1 is changed at an angle change rate W1y less than "1". The angle changing region R1y refers to a region between "−θ1a" and "−θ1c", which is less than "−θ1a", and a region between "θ1b" and "θ1d", which is greater than "θ1b". The coordinates in the angle changing region R1 are moved within a region extending between ±90° from the first center line CL1 by the expansion process and the compression process. Note that, the angle θ does not change at the angle change rate "1".

The angle change rate W1x is set to have the highest value when the angle θ1 is "0°". The angle change rate W1x is set to gradually decrease as the angle θ1 increases or decreases from "0°". The angle change rate W1y is set to always remain less than "1". In the case where the angle θ1 is between "−θ1c" and "−θ1a", the angle change rate Way is set to gradually decrease as the angle θ1 decreases from "−θ1a" to "−θ1e". The angle change rate W1y is set to gradually increase as the angle θ1 decreases from "−θ1e" to "−θ1c".

In like manner, in the case where the angle θ1 is between "θ1b" and "θ1d", the angle change rate W1y is set to gradually decrease as the angle θ1 increases from "θ1b" to "θ1f". The angle change rate W1y is set to gradually increase as the angle θ1 increases from "θ1f" to "θ1d".

Figure 7:
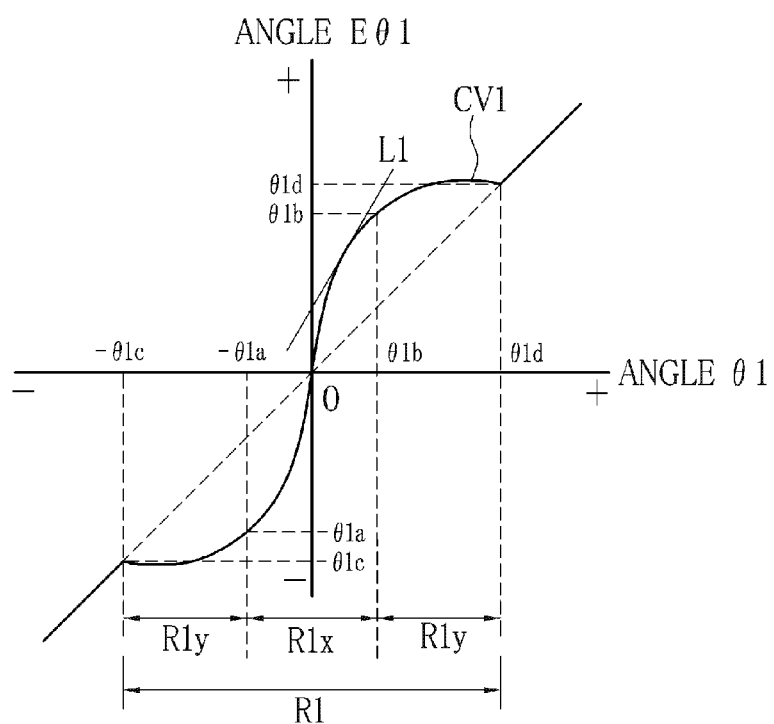
FIG. 7 is a graph illustrating a relationship between the angle θ1 and an angle Eθ1 after the first process for the signal ratio space.

By performing the first process (for the signal ratio space) composed of the expansion process and the compression process, as illustrated in FIG. 7, the angle θ1 on the positive side is changed to a positive angle Eθ1 that is greater than the angle θ1 while the angle θ1 on the negative side is changed to a negative angle Eθ1 that is smaller than the angle θ1. The angle change rate is represented by the inclination of the straight line "L1", being the tangent line of a curve CV1. The curve CV1 depicts the relationship between the angle θ1 and the angle Eθ1. The inclination of the straight line L1 is greater than "1" in the angle changing region R1x. On the other hand, the inclination of the straight line L1 is less than "1" in the angle changing region R1y. The angle θ of the coordinates outside the angle changing region R1 is changed to the angle Eθ that is equivalent to the angle θ (identical transformation). The inclination of the straight line L1 outside the angle changing region R1 is "1".

Figure 8:
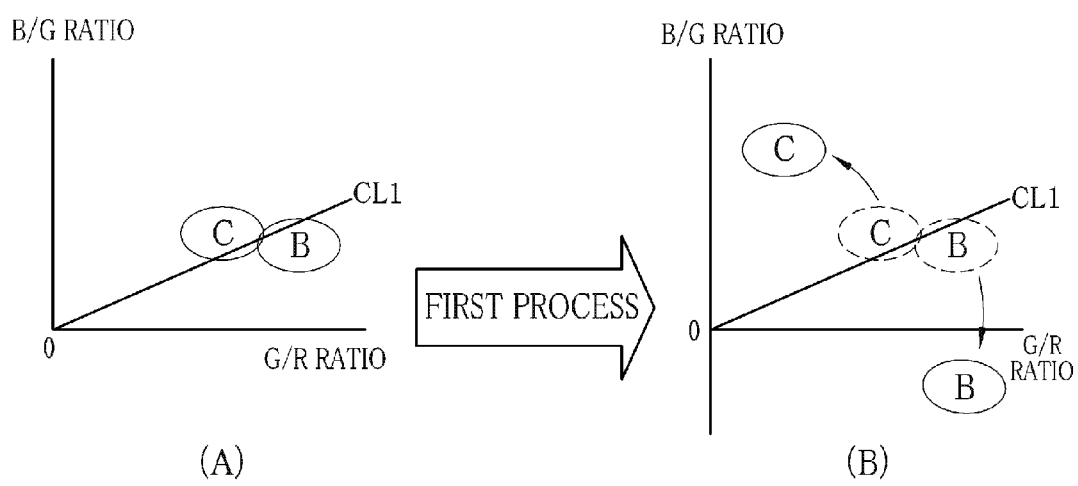
FIG. 8 is an explanatory view illustrating the operation and the effects of the first process for the signal ratio space.

The following operation and effects are obtained by changing the angle. As illustrated in a graph (A) in FIG. 8, before the first process (for the signal ratio space), the first observation area and the second observation area are close to each other, and some of them are mixed. After the first process, as illustrated in a graph (B) in FIG. 8, most of the coordinates corresponding to the first observation area are moved in the clockwise direction with respect to the first center line CL1 while most of the coordinates corresponding to the second observation area are moved in the counterclockwise direction with respect to the first center line CL. Thus, the difference between the first observation area and the second observation area is increased. In the first special image, in which the difference between the first observation area and the second observation area is increased, the difference in color of the object between the portion infected with the *H. pylori* and the portion in which the eradication of the *H. pylori* infection has been successful becomes distinct or apparent. Thereby, whether the eradication of the *H. pylori* infection has been successful is diagnosed reliably.

The region extending between ±90° from the first center line CL1 is a specific color region in which a difference in color (referred to as the "color difference" in this paragraph) of the object between a portion infected with the H. *Pylori* and a portion in which the eradication of the *H. pylori* infection has been successful is emphasized by changing the angle. In the region beyond (outside) the specific color region extending between ±90° from the first center line CL1, the color difference is not emphasized by changing the angle. For this reason, in the first process (for the signal ratio space), the compression process is performed in addition to the expansion process so that the angle Eθ1 after the expansion process or the compression process is within the specific color region extending between ±90° from the first center line CL1. Thus, in the first special image, the color difference in the specific color region is emphasized while the color difference in the region outside the specific color region is not emphasized.

Figure 9:
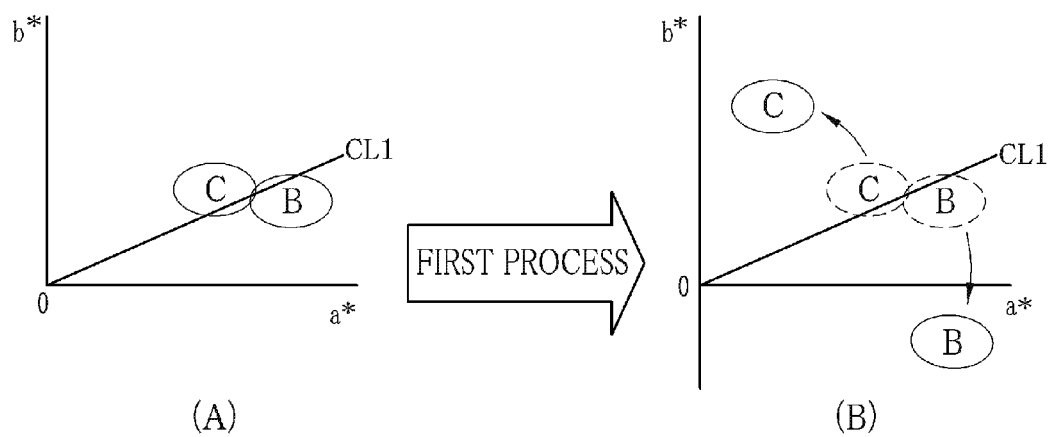
FIG. 9 is an explanatory view illustrating the operation and the effects of the first process in a case where a feature space is ab space.

Note that, as illustrated in FIG. 9, in the case of the feature space (ab space) formed by a* and b* (color components a* and b*, being the color information, in a CIE Lab space, the same hereinafter), which are obtained by the Lab conversion of the first RGB image signals performed by the Lab converter, most of the coordinates corresponding to the first observation area are moved in the clockwise direction while most of the coordinates in the second observation area are moved in the counterclockwise direction by the first process (for the ab space). Here, in FIG. 9, a graph (A) depicts the distribution of the first and second observation areas before the first process (for the ab space) and a graph (B) depicts the distribution of the first and second observation areas after the first process.

Figure 10:
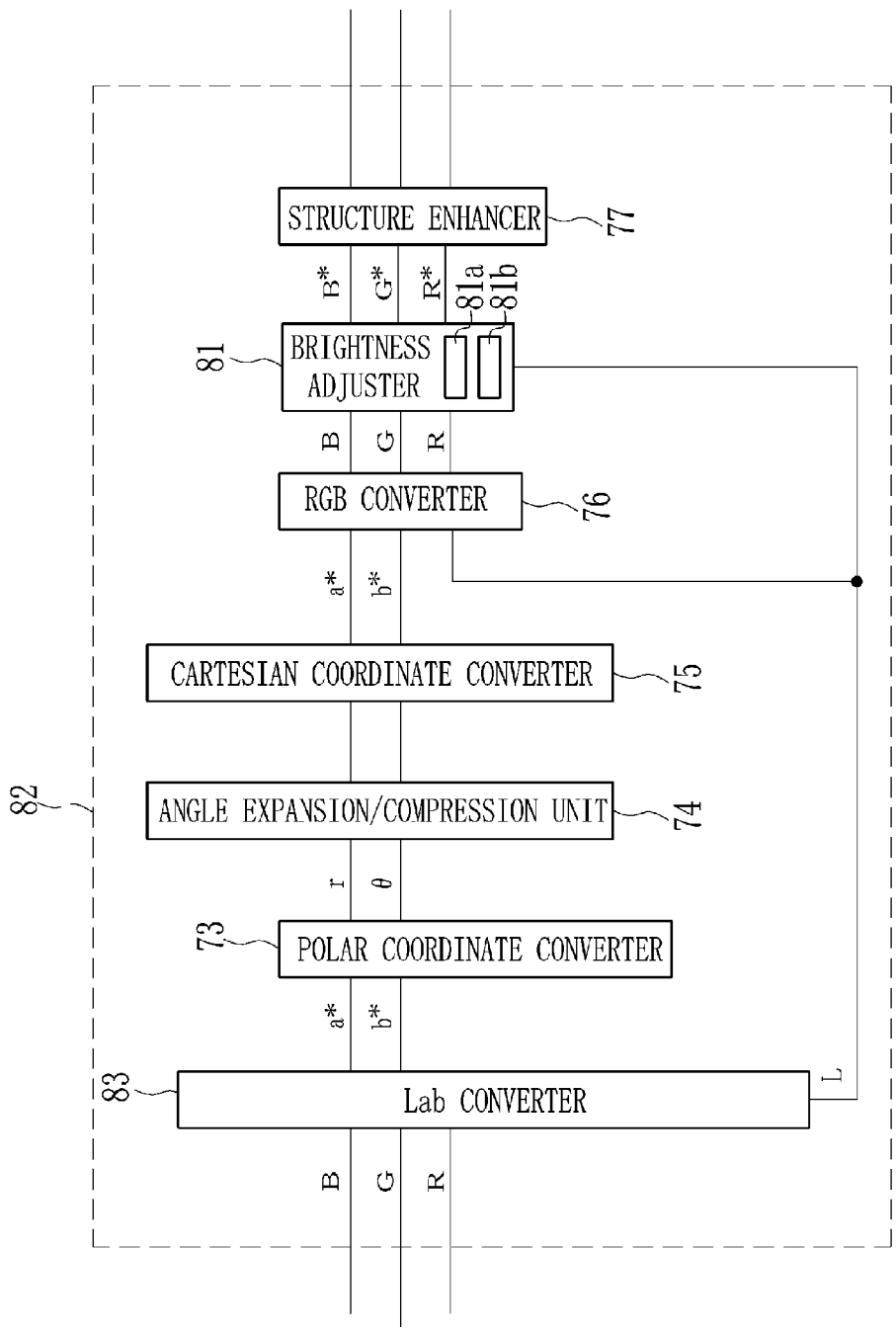
FIG. 10 is a block diagram illustrating functions of the special image processor used for the ab space.

Note that, in the case where the first process (for the ab space) is performed with the use of a* and b*, a special image processor 82 (see FIG. 10) is used. Unlike the special image processor 64, the special image processor 82 is not provided with the inverse gamma converter 70, the log converter 71, the signal ratio calculator 72, the inverse log converter 78, and the gamma converter 79. Instead, the special image processor 82 comprises a Lab converter 83, which corresponds to the "color information obtaining section" of the present invention. The components, other than those described above, of the special image processor 82 are the same as or similar to the components of the special image processor 64.

The Lab converter 83 converts the first RGB image signals into L, a*, and b* through the well-known Lab conversion. The "L" is transmitted to the RGB converter 76 and the brightness adjuster 81. The "a*" and "b*" are transmitted to the polar coordinate converter 73. The RGB converter 76 converts the "a*" and "b*", which have passed through the Cartesian coordinate converter 75, and the "L" into the second RGB image signal. The first brightness information calculator 81a of the brightness adjuster 81 converts the "L", which is transmitted from the Lab converter 83, into a luminance signal Y with the use of a predetermined conversion equation. The converted luminance signal Y is referred to as the first brightness information Yin. The second brightness information calculator 81b calculates the second brightness information Yout from the second RGB image signal. The brightness adjuster 81 uses the first brightness information Yin and the second brightness information Yout to adjust the pixel values of the second RGB image signals. Note that the method for calculating the second brightness information Yout and the method for adjusting the pixel values of the second RGB image signals are the same as or similar to those of the special image processor 64.

Figure 11:
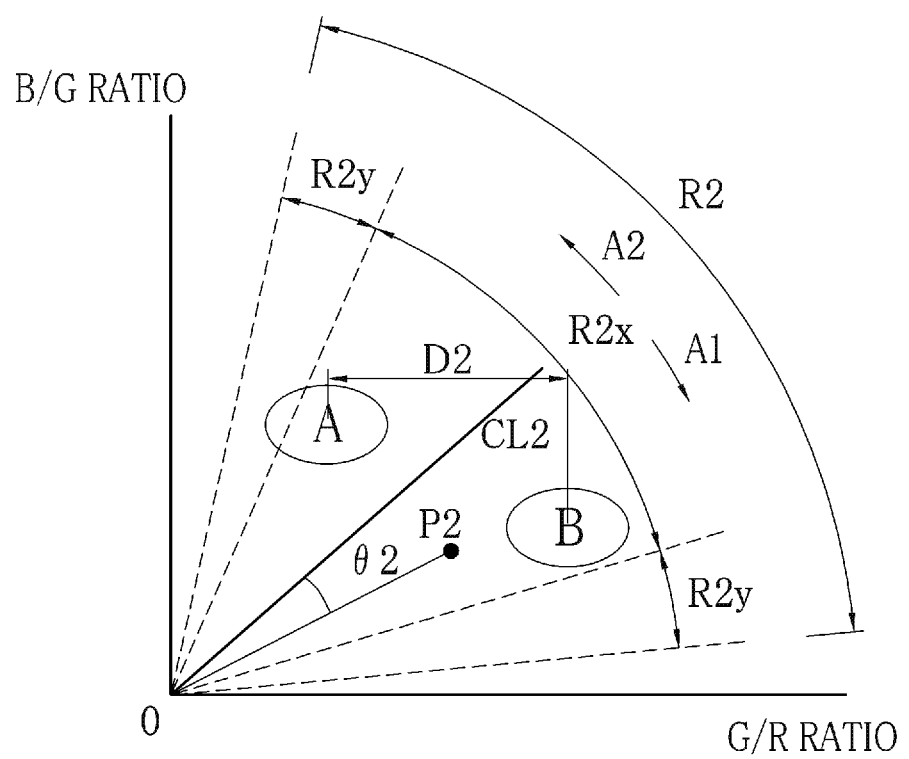
FIG. 11 is an explanatory view illustrating a second process for the signal ratio space.

As illustrated in FIG. 11, in the second process (for the signal ratio space), a region including the first observation area (denoted as "B") and the third observation area (denoted as "A" in FIG. 11 and so forth) is set as an angle changing region R2 in the signal ratio space. In the first observation area, the coordinates corresponding to a portion (of the object) infected with the $H.$ $pylori$ are distributed. In the third observation area, the coordinates corresponding to a portion (of the object) uninfected with the $H.$ $pylori$ are distributed. The angle $\theta$ of the coordinates within the angle changing region R2 is changed while the angle $\theta$ of the coordinates outside the angle changing region R2 is not changed. In the second process (for the signal ratio space), the radial coordinate r of the coordinates within the angle changing region R2 is not changed. Note that there is a distance D2 between the average value of the first observation area and the average value of the third observation area. The distance D2 is greater than the distance D1 between the average value of the first observation area and the average value of the second observation area.

In the angle changing region R2, a second center line CL2 is set between the first observation area and the third observation area. The angle changing region R2 is greater in size than the angle changing region R1. The inclination of the second center line CL2 in the signal ratio space is greater than that of the first center line CL1. Coordinates (point) P2 in the angle changing region R2 are defined by an angle $\theta 2$ from the second center line CL2. The angle $\theta 2$ located in the clockwise direction A1 from the second center line CL2 is defined as a positive angle. The angle $\theta 2$ located in the counterclockwise direction A2 from the second center line CL2 is defined as a negative angle.

Figure 12:
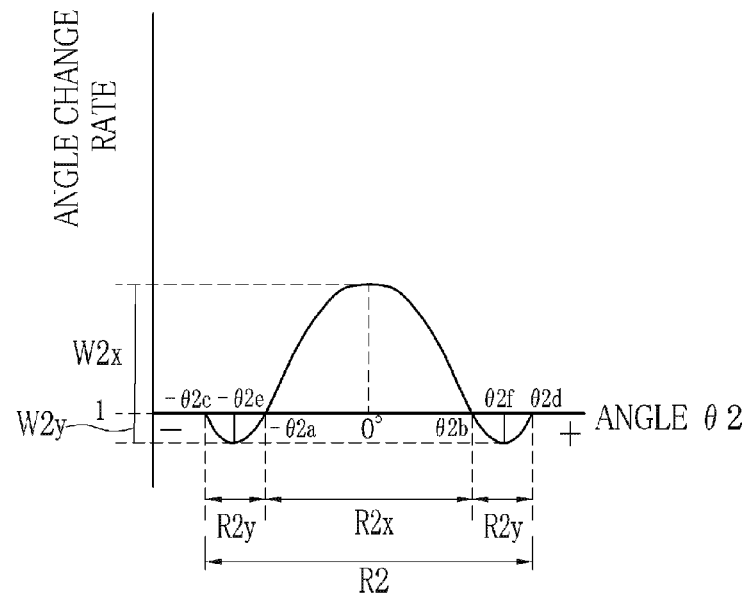
FIG. 12 is a graph illustrating a relationship between an angle θ2 and an angle change rate in the second process for the signal ratio space.

As illustrated in FIG. 12, in the second process (for the signal ratio space), the expansion process is performed on the angle $\theta 2$ in an angle changing region R2$x$, which contains the second center line CL2 and extends within the angle changing region R2. In the expansion process, the angle $\theta 2$ is changed at an angle change rate W2$x$ that is greater than "1". The angle changing area R2$x$ refers to a region between "$-\theta 2a$" and "$\theta 2b$". In an angle changing region R2$y$ outside the angle changing region R2$x$, the compression process is performed. In the compression process, the angle $\theta 2$ is changed at an angle change rate W2$y$ that is less than "1". The angle changing area R2$y$ refers to a region between "$-\theta 2a$" and "$-\theta 2c$", which is less than "$-\theta 2a$", and a region between "$\theta 2b$" and "$\theta 2d$", which is greater than "$\theta 2b$". The coordinates in the angle changing region R2 are moved within a region extending between ±90° from the second center line CL2 by the expansion process and the compression process. Note that the angle $\theta$ does not change at the angle change rate "1".

The angle change rate W2$x$ is set to have the highest value when the angle $\theta 2$ is "0°". It is preferred that the angle change rate W2$x$ at the angle $\theta 2$ of 0° is less than the angle change rate W1$x$ at the angle $\theta 1$ of 0°. The angle change rate W2$y$ is set to always remain less than "1". In the case where the angle $\theta 2$ is between "$-\theta 2c$" and "$-\theta 2a$", the angle change rate W2$y$ is set to gradually decrease as the angle $\theta 2$ decreases from "$-\theta 2a$" to "$-\theta 2e$". The angle change rate W2$y$ is set to gradually increase as the angle $\theta 2$ decreases from "$-\theta 2e$" to "$-\theta 2c$".

In like manner, in the case where the angle $\theta 2$ is between "$\theta 2b$" and "$\theta 2d$", the angle change rate W2$y$ is set to gradually decrease as the angle $\theta 2$ increases from "$\theta 2b$" to "$\theta 2f$". The angle change rate W2$y$ is set to gradually increase as the angle $\theta 2$ increases from "$\theta 2f$" to "$\theta 2d$".

Figure 13:
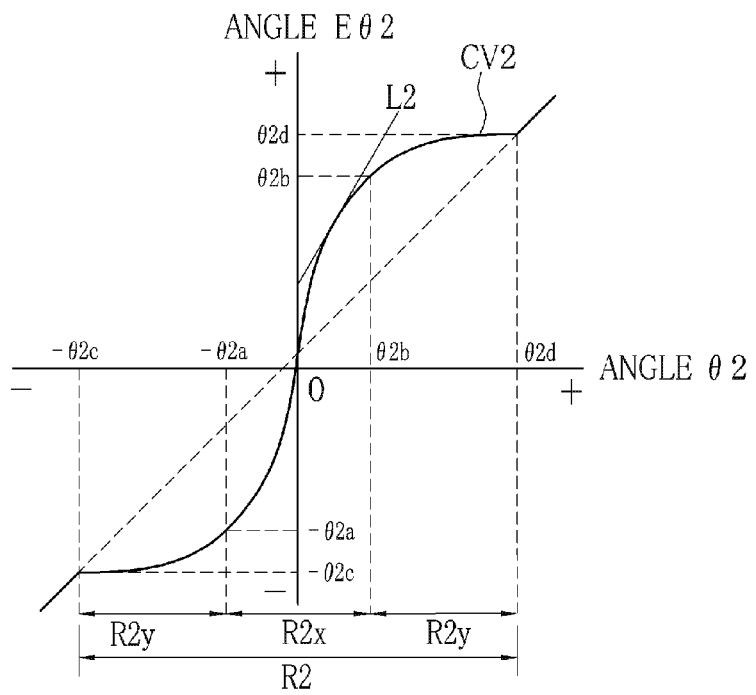
FIG. 13 is a graph illustrating a relationship between the angle θ2 and an angle Eθ2 obtained after the second process for the signal ratio space.

By performing the second process (for the signal ratio space) composed of the expansion process and the compression process, as illustrated in FIG. 13, the angle $\theta 2$ on the positive side is changed to a positive angle E$\theta 2$ that is greater than the angle $\theta 2$ while the angle $\theta 2$ on the negative side is changed to a negative angle E$\theta 2$ that is smaller than the angle $\theta 2$. The angle change rate is represented by the inclination of the straight line "L2", being the tangent line of a curve CV2. The curve CV2 depicts the relationship between the angle $\theta 2$ and the angle E$\theta 2$. The inclination of the straight line L2 is greater than "1" in the angle changing region R2$x$. On the other hand, the inclination of the straight line L2 is less than "1" in the angle changing region R2$y$. The angle $\theta$ of the coordinates outside the angle changing region R2 is changed to the angle E$\theta$ that is equivalent to the angle $\theta$ (identical transformation). The inclination of the straight line L2 outside the angle changing region R2 is "1".

Figure 14:
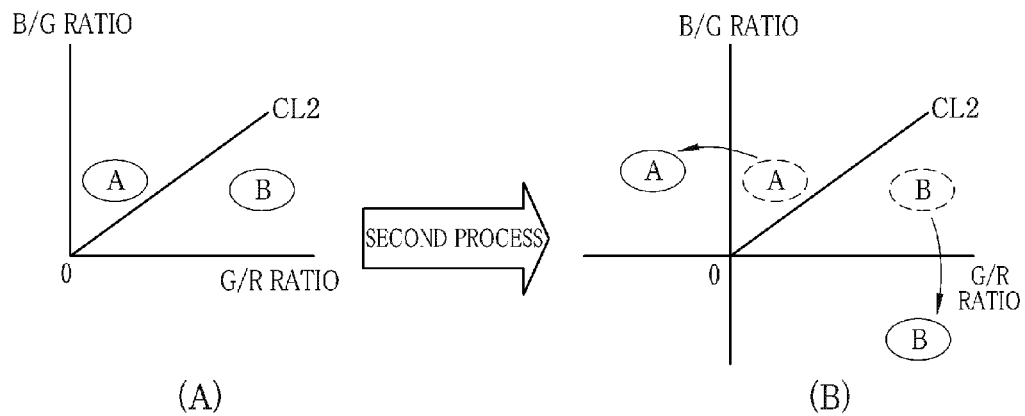
FIG. 14 is an explanatory view illustrating the operation and the effects of the second process for the signal ratio space.

The following operation and the effects are obtained by changing the angle as described above. Before the second process (for the signal ratio space), as illustrated in a graph (A) in FIG. 14, the first observation area and the third observation area are located in the first quadrant of the signal ratio space. After the second process, as illustrated in a graph (B) in FIG. 14, most of the coordinates corresponding to the first observation area are moved in the clockwise direction with respect to the second center line CL2. Most of the coordinates corresponding to the third observation area are moved in the counterclockwise direction with respect to the second center line CL2. Thereby most of the coordinates corresponding to the first observation area are moved to the fourth quadrant of the signal ratio space. Most of the coordinates corresponding to the third observation area are moved to the second quadrant of the signal ratio space. Thus, the difference between the first observation area and the third observation area is further increased. In the second special image, which is produced by further increasing the difference between the first observation area and the third observation area, the difference in color of the object between a portion infected with the $H.$ $pylori$ and a portion uninfected with the $H.$ $pylori$ is distinct or apparent. As a result, the infection with the $H.$ $pylori$ is diagnosed reliably.

In the second process (for the signal ratio space), the compression process is performed in addition to the expansion process so that the angle E$\theta 2$ after the expansion process or the compression process is within a specific color region extending between ±90° from the second center line CL2. Thereby the color difference is emphasized in the specific color region in the second special image. In the color region other than the specific color region, the color difference is not emphasized.

Figure 15:
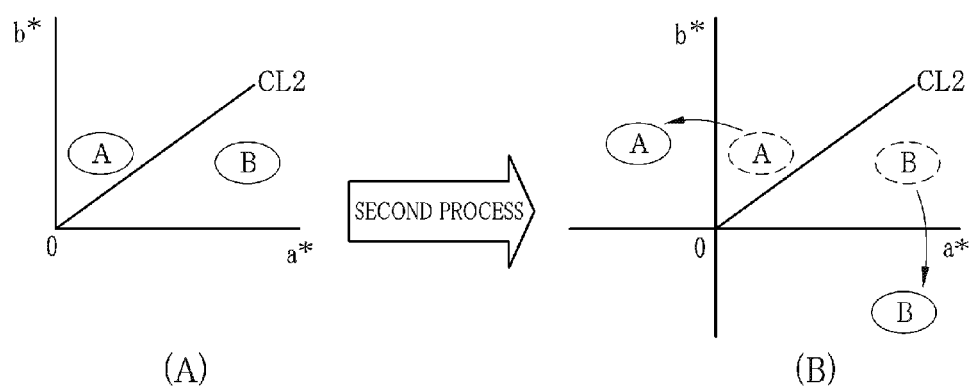
FIG. 15 is an explanatory view illustrating the operation and the effects of the second process in a case where the feature space is the ab space.

Note that, as illustrated in FIG. 15, in the case of the feature space (the ab space) formed by a* and b* (the color components a* and b*, being the color information, in the CIE Lab space), which are obtained by the Lab conversion of the first RGB image signals performed by the Lab converter, most of the coordinates corresponding to the first observation area are moved in the clockwise direction while most of the coordinates in the third observation area are moved in the counterclockwise direction by the second process (for the ab space). Note that the special image processor 82 (FIG. 10) performs the Lab conversion.

Figure 16:
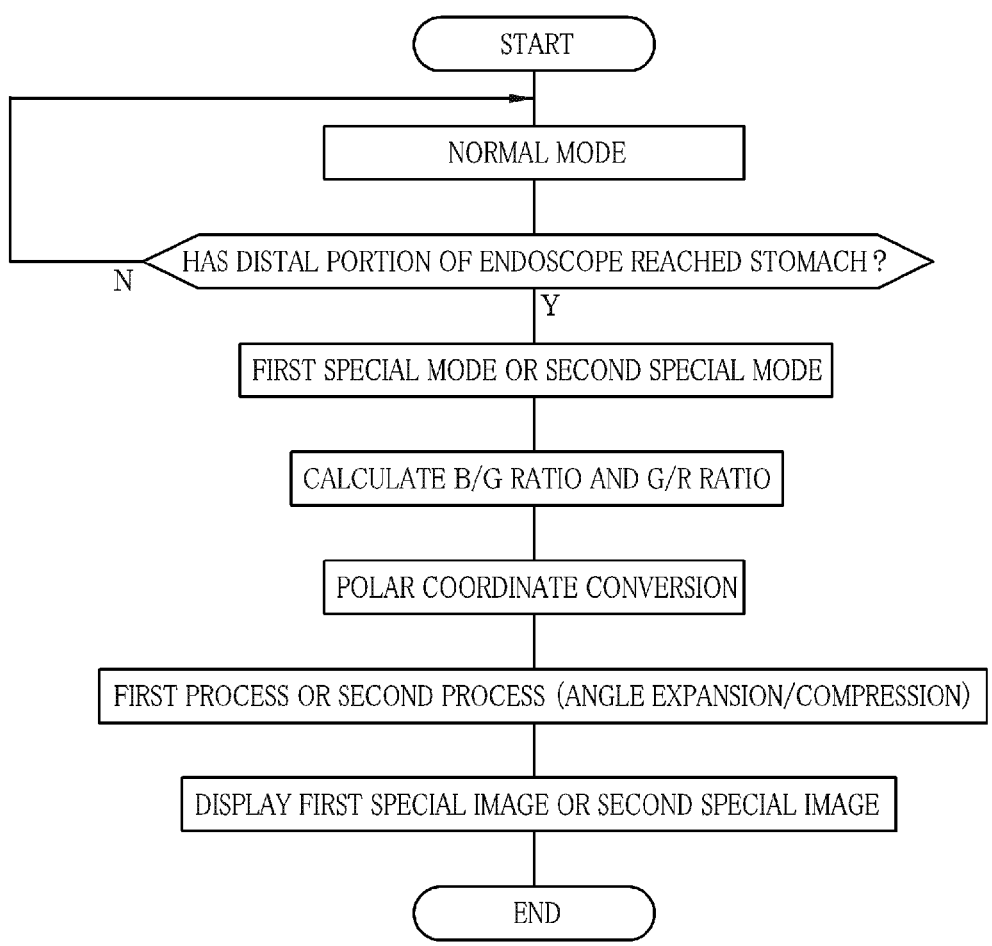
FIG. 16 is a flowchart illustrating steps in an example of the invention.

Hereinafter, referring to a flowchart in FIG. 16, an operation of the present invention is described. First, the mode is set to the normal mode. The insertion section 12a of the endoscope 12 is inserted into the body cavity. After the distal portion 12d of the insertion section 12a reached the stomach, the mode SW 13a is operated to switch from the normal mode to the first or second special mode. To diagnose whether the eradication of the *H. pylori* has been successful, the mode is switched to the first special mode. To diagnose whether the patient is infected with the *H. pylori*, the mode is switched to the second special mode.

The signal ratio calculator 72 calculates the B/G ratio and the G/R ratio based on the RGB image signals obtained after the mode is switched to the first or second special mode. Then, the B/G ratio and the G/R ratio are converted into the radial coordinate r and the angular coordinate θ through the polar coordinate conversion.

Next, in the first special mode, the angle expansion/compression unit 74 performs the first process (for the signal ratio space). In the first process, the difference between the first observation area and the second observation area is increased. In the first observation area, the radial coordinates r and the angular coordinates θ corresponding to the portion (of the object) infected with the *H. pylori* are distributed. In the second observation area, the radial coordinates r and the angular coordinates θ corresponding to the portion (of the object) in which the eradication of the *H. pylori* infection has been successful are distributed. In the second special mode, the angle expansion/compression unit 74 performs the second process (for the signal ratio space). In the second process, the difference between the first observation area and the third observation area is increased. In the first observation area, the radial coordinates r and the angular coordinates θ corresponding to the portion (of the object) infected with the *H. pylori* are distributed. In the third observation area, the radial coordinates r and the angular coordinates θ corresponding to the portion (of the object) uninfected with the *H. pylori* are distributed. Based on the radial coordinates r and the angular coordinates θ subjected to the first or second process (for the signal ratio space) by the angle expansion/compression unit 74, the first special image or the second special image is produced. The produced first or second special image is displayed on the monitor 18.

Note that, in the above embodiment, the signal ratio calculator 72 calculates the B/G ratio and the G/R ratio based on the first RGB image signals. The first or second process is performed in the feature space formed by the B/G ratio and the G/R ratio. Alternatively, color information which differs from the B/G ratio and the G/R ratio may be obtained. The first or second process may be performed in a feature space formed by the different color information.

Figure 17:
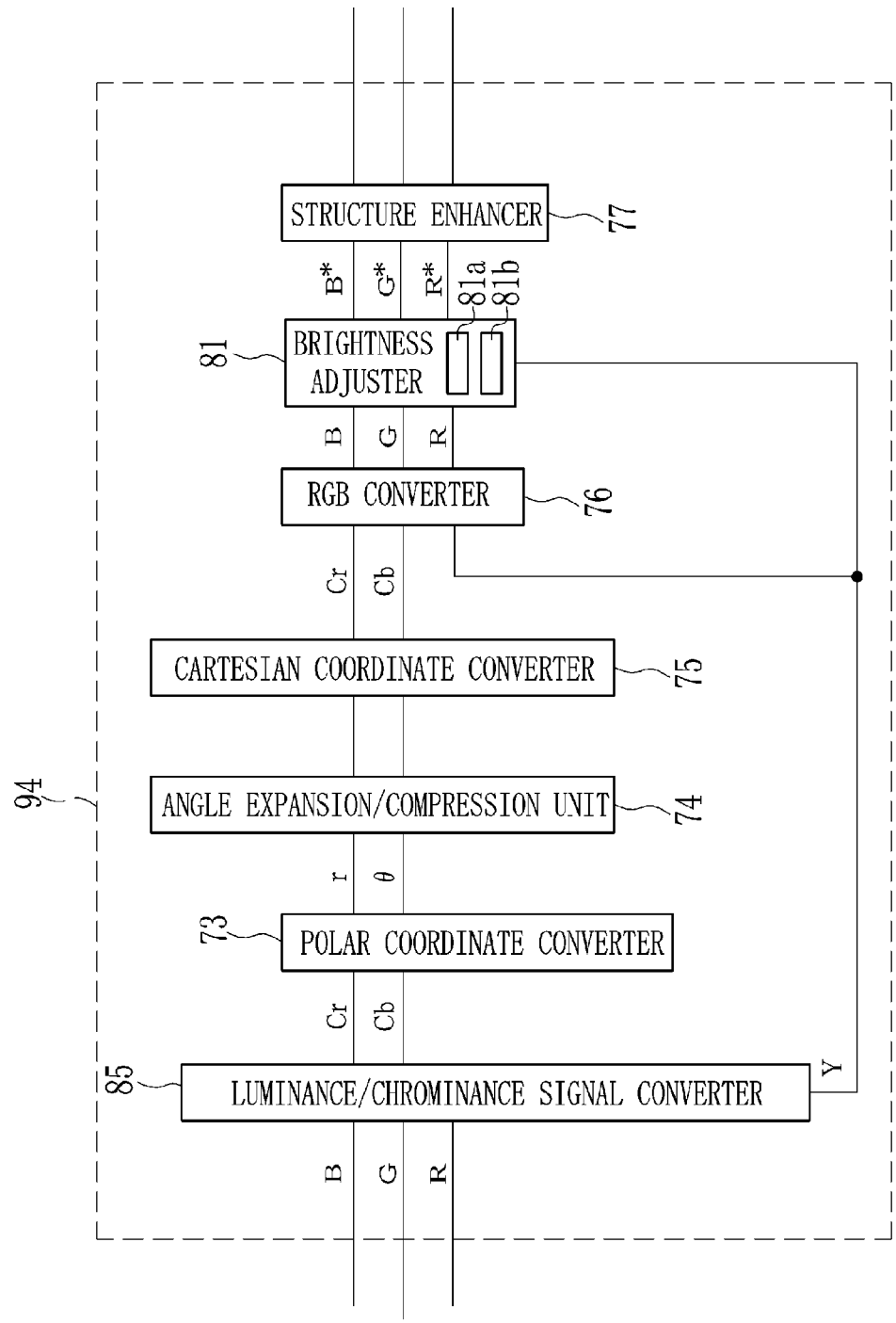
FIG. 17 is a block diagram illustrating functions of the special image processor used in a case where the feature space is formed by chrominance signals Cr and Cb.

For example, chrominance signals Cr and Cb may be obtained as the color information. The first or second process may be performed in a feature space formed by the chrominance signals Cr and Cb. In the case where the special image is produced by using the chrominance signals Cr and Cb, a special image processor 94 illustrated in FIG. 17 is used. Unlike the special image processor 64, the special image processor 94 is not provided with the inverse gamma converter 70, the log converter 71, the signal ratio calculator 72, the inverse log converter 78, and the gamma converter 79. Instead, the special image processor 94 comprises a luminance/chrominance signal converter 85. The components, other than those described above, of the special image processor 94 are the same as or similar to the components of the special image processor 64.

The luminance/chrominance signal converter 85, which corresponds to the "color information obtaining section" of the present invention, converts the first RGB image signals into the luminance signal Y and the chrominance signals Cr and Cb. A well-known conversion equation is used for the conversion into the chrominance signals Cr and Cb. The chrominance signals Cr and Cb are transmitted to the polar coordinate converter 73. The luminance signal Y is transmitted to the RGB converter 76 and the brightness adjuster 81. The RGB converter 76 converts the chrominance signals Cr and Cb, which passed through the Cartesian coordinate converter 75, and the luminance signal Y into the second RGB image signals. The brightness adjuster 81 adjusts the pixel values of the second RGB image signals with the use of the luminance signal Y (the first brightness information Yin) and the second brightness information (the second brightness information Yout) which is calculated by the second brightness information calculator 81b. Note that the method for calculating the second brightness information Yout and the method for adjusting the pixel values of the second RGB image signals are the same as or similar to those of the special image processor 64.

Figure 18:
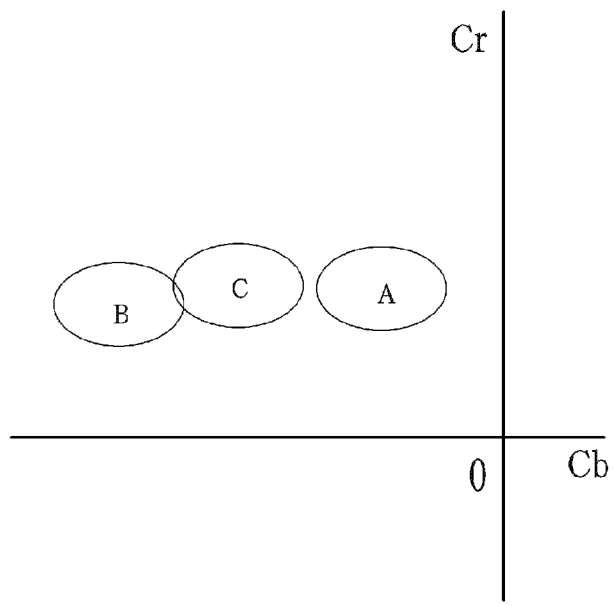
FIG. 18 is an explanatory view illustrating distribution "A" of coordinates corresponding to a portion uninfected with *Helicobacter pylori* (*H. pylori*), distribution "B" of coordinates corresponding to a portion infected with the *H. pylori*, and distribution "C" of coordinates corresponding to a portion in which the *H. pylori* infection has been successfully eradicated, in the feature space (the vertical axis: Cb, the horizontal axis: Cr)

The special image processor 94 performs the first process or the second process (for the Cb-Cr space) in the feature space (hereinafter referred to as the Cb-Cr space; the vertical axis: the chrominance signal Cr, the horizontal axis: the chrominance signal Cb). In the Cb-Cr space, as illustrated in FIG. 18, the third observation area (denoted as "A") is closest to the vertical axis Cr. The second observation area (denoted as "C") is second closest to the vertical axis Cr. The first observation area (denoted as "B") is farthest from the vertical axis Cr.

Figure 19:
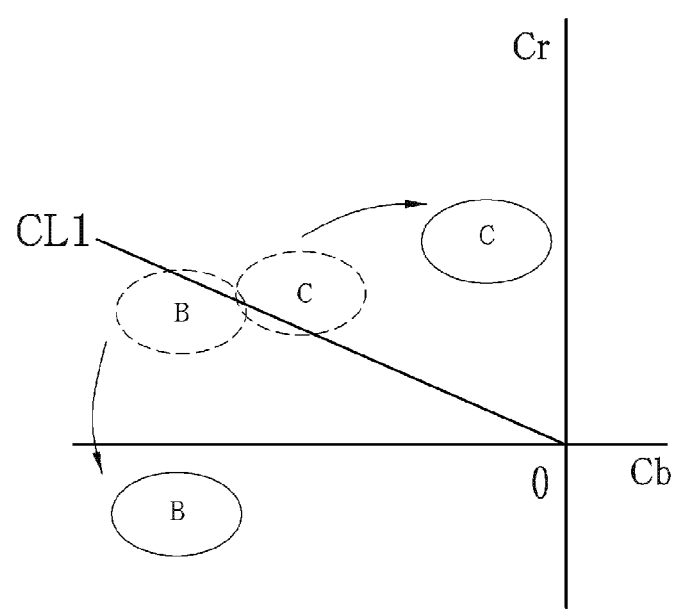
FIG. 19 is an explanatory view illustrating the first process in a case where the feature space is formed by the chrominance signals Cr and Cb.

In the first process (for the Cb-Cr space), as illustrated in FIG. 19, the angle expansion/compression unit 74 expands or compresses the angle of the coordinates in the first observation area (denoted as "B"), which is located on one of the sides of the first center line CL1, in the counterclockwise direction. The angle expansion/compression unit 74 expands or compresses the angle of the coordinates in the second observation area (denoted as "C"), which is located on the other side of the first center line CL1, in the clockwise direction. The methods for expanding and compressing the angles in the first and second observation areas in the Cb-Cr space are the same as or similar to those in the signal ratio space (see FIGS. 5 to 8). Note that, in FIG. 19, the areas with dotted lines illustrate the areas before the first process (for the Cb-Cr space). The areas with solid lines illustrate the areas after the first process. This also applies to the drawings described below.

Figure 20:
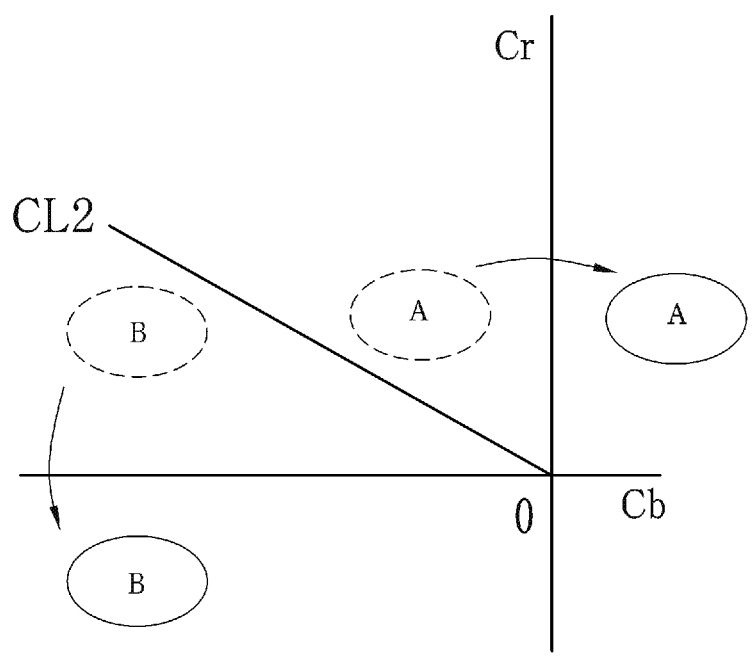
FIG. 20 is an explanatory view illustrating the second process in the case where the feature space is formed by the chrominance signals Cr and Cb.

In the second process (for the Cb-Cr space), as illustrated in FIG. 20, the angle expansion/compression unit 74 expands or compresses the angle of the coordinates in the first observation area (denoted as "B"), which is located on one of the sides of the second center line CL2, in the counterclockwise direction. The angle expansion/compression unit 74 expands or compresses the angle of the coordinates in the third observation area (denoted as "A"), which is located on the other side of the second center line CL2, in the clockwise direction. The methods for expanding and compressing the angles in the first and third observation areas in the Cb-Cr space are the same as or similar to those in the signal ratio space (see FIGS. 11, 12, 13, and 14).

Figure 21:
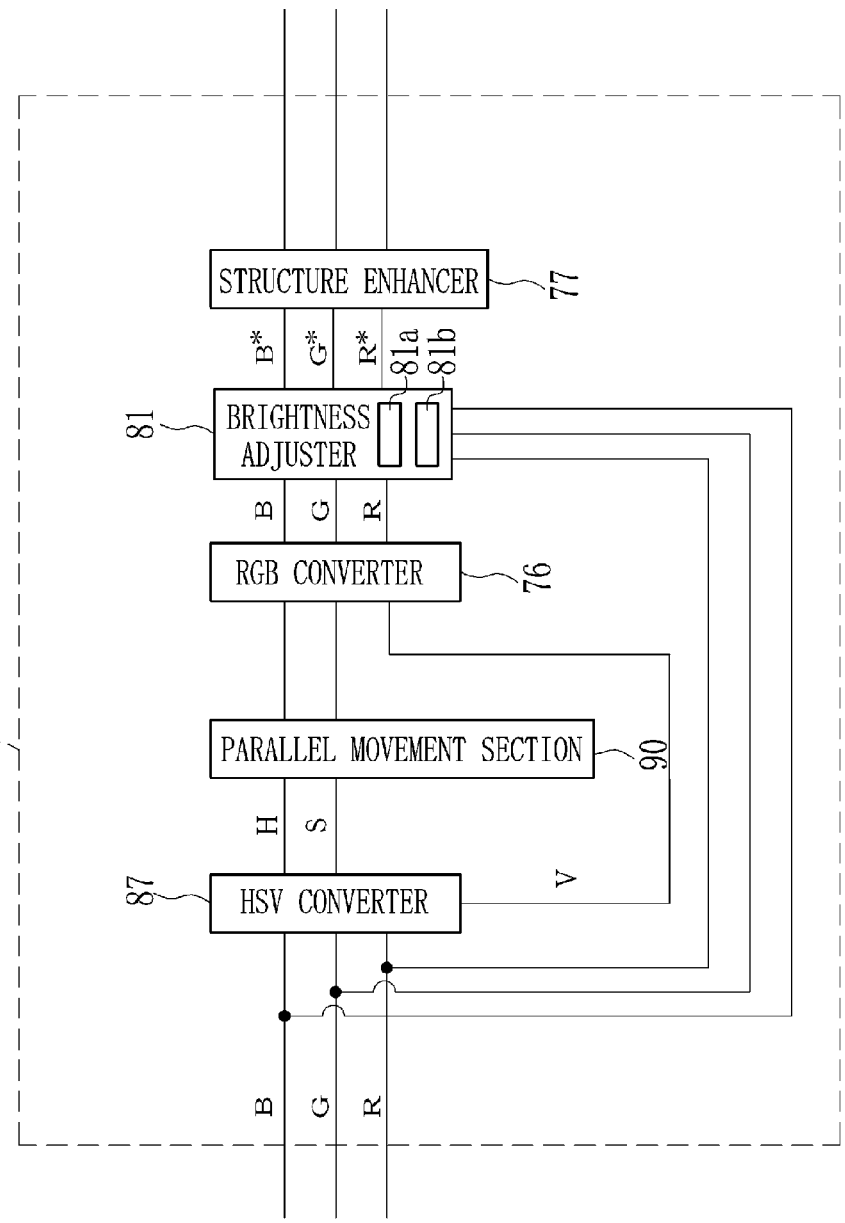
FIG. 21 is a block diagram illustrating functions of the special image processor in a case where the feature space is formed by hue H and saturation S.

Hue H and saturation S may be obtained and used as the color information. The first or second process may be performed in the feature space formed by the hue H and the saturation S. In the case where the hue H and the saturation S are used to produce the special image, the special image processor 94 illustrated in FIG. 21 is used. Unlike the special image processor 64, the special image processor 94 is not provided with the inverse gamma converter 70, the log converter 71, the signal ratio calculator 72, the polar coordinate converter 73, the angle expansion/compression unit 74, the Cartesian coordinate converter 75, the inverse log converter 78, and the gamma converter 79. Instead, the special image processor 94 comprises an HSV converter 87 and a parallel movement section 90. The components, other than those described above, of the special image processor 94 are the same as or similar to the components of the special image processor 64.

The HSV converter 87, which corresponds to the "color information obtaining section" of the present invention, converts the first RGB image signals into hue H, saturation S, and value V. A well-known conversion equation is used for the conversion into the hue H, the saturation S, and the value V. The hue H and the saturation S are transmitted to the parallel movement section 90. The value V is transmitted to the RGB converter 76. The RGB converter 76 converts the hue H and the saturation S, which passed through the parallel movement section 90, and the value V into the second RGB image signals. The brightness adjuster 81 adjusts the pixel values of the second RGB image signals with the use of the first brightness information Yin calculated by the first brightness information calculator 81a and the second brightness information Yout calculated by the second brightness information calculator 81b. Note that the methods for calculating the first brightness information Yin and the second brightness information Yout and the method for adjusting the pixel values of the second RGB image signals are the same as or similar to those of the special image processor 64.

Figure 22:
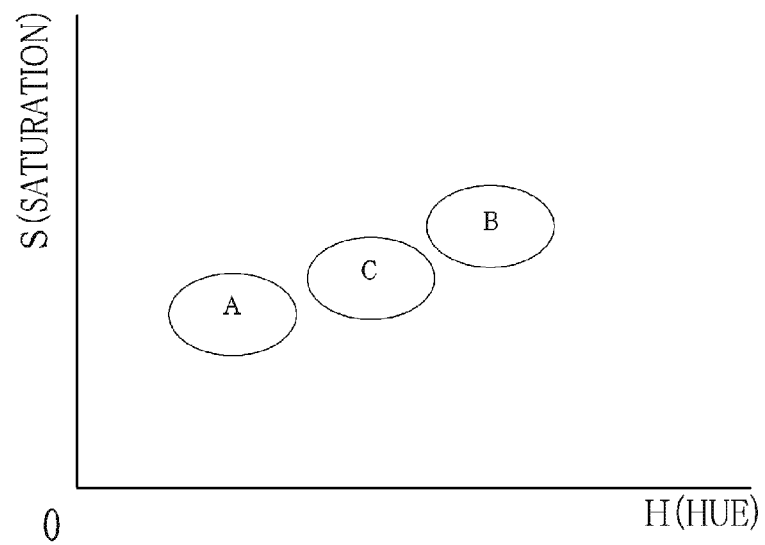
FIG. 22 is an explanatory view illustrating the distribution "A" of the coordinates corresponding to the portion uninfected with the *H. pylori*, the distribution "B" of the coordinates corresponding to the portion infected with the *H. pylori*, and the distribution "C" of the coordinates corresponding to the portion in which the *H. pylori* infection has been successfully eradicated in the feature space (the vertical axis: saturation S, the horizontal axis: hue H)

The special image processor 94 performs the first process or the second process (for HS space) in the feature space (hereinafter referred to as the HS space; the vertical axis: the saturation S, the horizontal axis: the hue H). As illustrated in FIG. 22, the positions (or distribution) of the first observation area (denoted as "B"), the second observation area (denoted as "C"), and the third observation area (denoted as "A") in the HS space slightly differ from those in the signal ratio space (the vertical axis: the B/G ratio, the horizontal axis: the G/R ratio).

Figure 23:
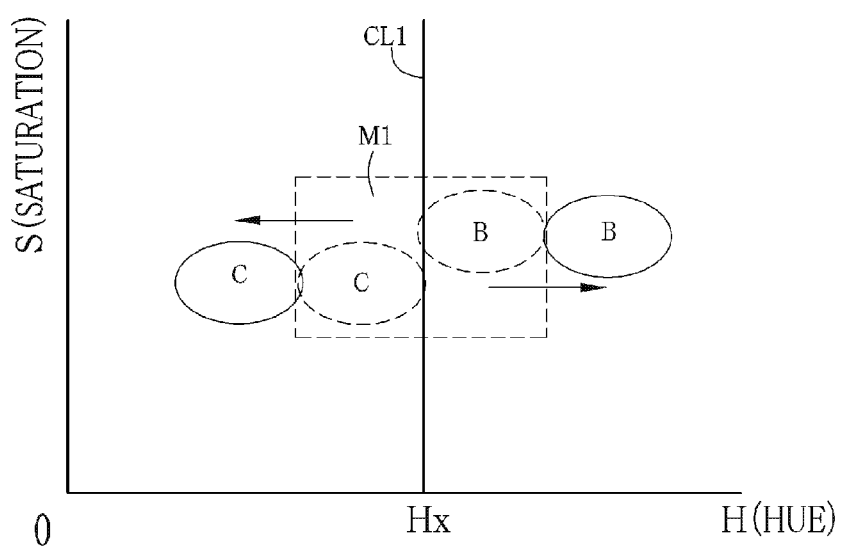
FIG. 23 is an explanatory view illustrating the first process for the feature space formed by the hue H and the saturation S.

As illustrated in FIG. 23, in the first process (for the HS space), the parallel movement section 90 translates or moves the coordinates in the first observation area, which is located on one of the sides of the first center line CL1, laterally (or parallel to themselves) to the right in the hue direction. The parallel movement section 90 translates or moves the coordinates in the second observation area, which is located on the other side of the first center line CL1, laterally (or parallel to themselves) to the left in the hue direction. Thus, the difference between the coordinates corresponding to the first observation area and the coordinates corresponding to the second observation area is increased. Note that the first center line CL1 is provided to a portion, between the first observation area and the second observation area in the HS space, in which the hue H takes a value Hx (a constant). It is preferred that the parallel movement section 90 translates or moves the coordinates in a first movement area M1, which includes the first observation area and the second observation area, laterally or parallel.

Figure 24:
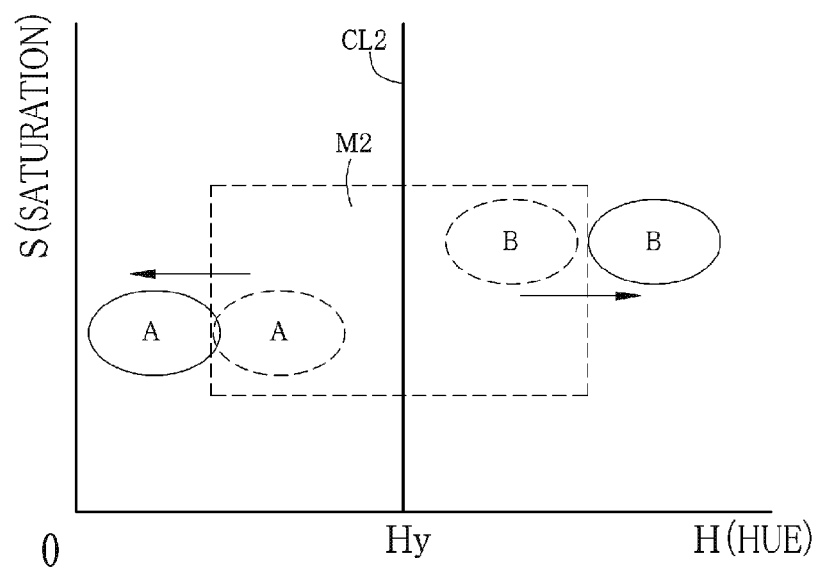
FIG. 24 is an explanatory view illustrating the second process for the feature space formed by the hue H and the saturation S.

As illustrated in FIG. 24, in the second process (for the HS space), the parallel movement section 90 translates or moves the coordinates in the first observation area, which is located on one of the sides of the second center line CL2, laterally (or parallel to themselves) to the right in the hue direction. The parallel movement section 90 translates or moves the coordinates in the third observation area, which is located on the other side of the second center line CL2, laterally (or parallel to themselves) to the left in the hue direction. Thus, the difference between the coordinates corresponding to the first observation area and the coordinates corresponding to the third observation area is increased. Note that the second center line CL2 is provided to a portion, between the first observation area and the second observation area in the HS space, in which the hue H takes a value Hy (a constant) that is different from the value Hx of the first center line CL1. It is preferred that the parallel movement section 90 translates or moves the coordinates in a second movement area M2, which includes the first observation area and the third observation area, laterally or parallel. The second movement area M2 is greater in size than the first movement area M1.

(Second Embodiment)

In the second embodiment, a laser and a phosphor are used, instead of the LEDs 20a to 20d of the four colors described in the first embodiment, to illuminate the object. Other than that, the configuration is the same as or similar to that in the first embodiment.

Figure 25:
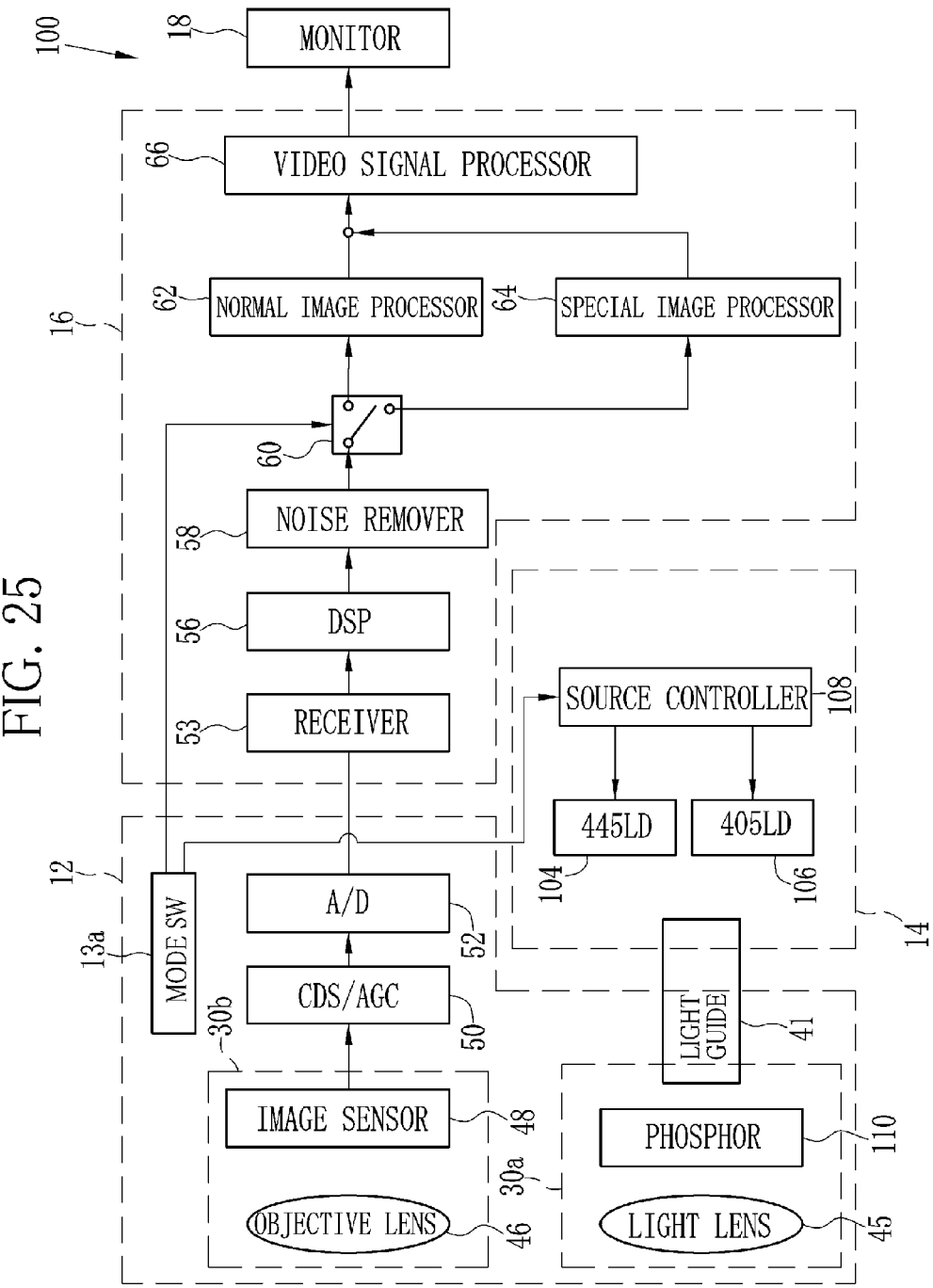
FIG. 25 is a block diagram illustrating functions of an endoscope system according to a second embodiment.

As illustrated in FIG. 25, in the light source device 14 of an endoscope system 100 according to the second embodiment, a blue laser (denoted as 445LD in FIG. 25) 104 and a blue-violet laser (denoted as 405LD in FIG. 25) 106 are provided in place of the LEDs 20a to 20d of the four colors. The blue laser 104 emits blue laser beams with the center wavelength 445±10 nm. The blue-violet laser 106 emits blue-violet laser beams with the center wavelength 405±10 nm. The light emissions from the semiconductor light emitting elements of the lasers 104 and 106 are controlled individually by a source controller 108. The light quantity ratio between the light (laser beams) from the blue laser 104 and the light (laser beams) from the blue-violet laser 106 is changed as desired.

In the normal mode, the source controller 108 actuates the blue laser 104. In the first or second special mode, the source controller 108 actuates both the blue laser 104 and the blue-violet laser 106 such that the light-emission ratio of the blue laser beams is greater than that of the blue-violet laser beams. The laser beams emitted from each of the lasers 104 and 106 are incident on the light guide (LG) 41 through optical members (e.g. a condenser lens, an optical fiber, a combiner, and the like, all not shown).

Note that the full width at half maximum of the blue laser beams or the blue-violet laser beams is preferred to be in the order of ±10 nm. Broad-area type InGaN-based laser diodes may be used for the blue laser 104 and blue-violet laser 106. The InGaNAs-based laser diodes or the GaNAs-based laser diodes may be used instead. A light emitting element such as a light emitting diode may be used as the light source.

The illumination optical system 30a is provided with the light lens 45 and a phosphor 110 on which the blue laser beams or the blue-violet laser beams from the light guide 41 are incident. The emission of the blue laser beams causes the phosphor 110 to emit fluorescence. A part of the blue laser beams passes through the phosphor 110. The blue-violet laser beams pass through the phosphor 110 without exciting the phosphor. The light from the phosphor 110 is applied to the object through the light lens 45.

Figure 26:
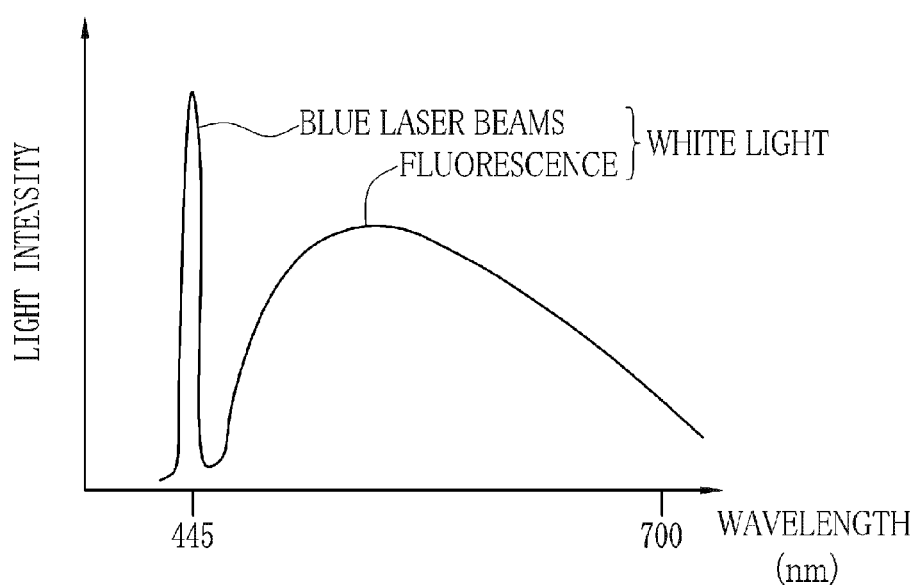
FIG. 26 is a graph illustrating an emission spectrum of white light.
Figure 27:
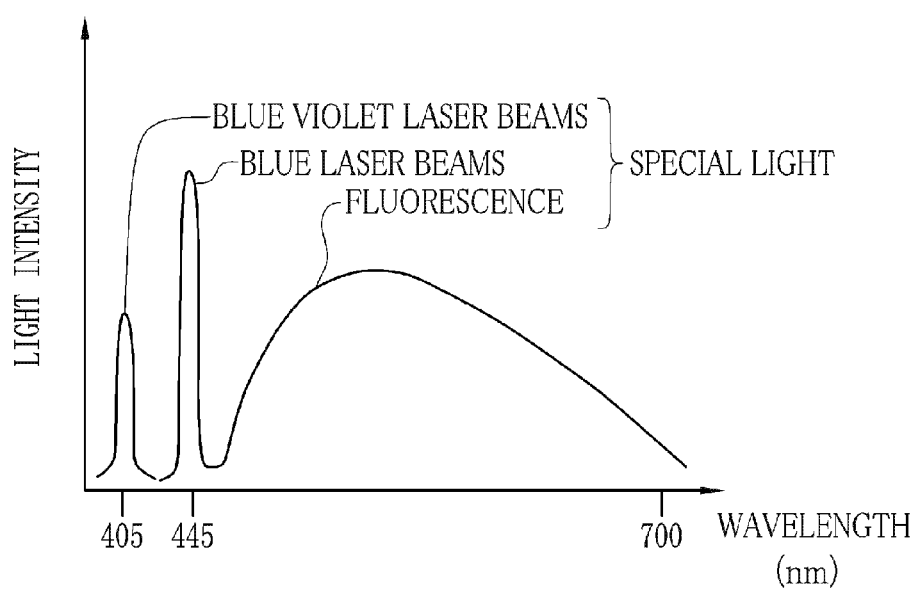
FIG. 27 is a graph illustrating an emission spectrum of special light.

Here, in the normal mode, the blue laser beams are mostly incident on the phosphor 110, so that the white light, being the combination of the blue laser beams and the fluorescence from the phosphor 110 excited by the blue laser beams, is applied to the object as illustrated in FIG. 26. In the first or second special mode, both the blue-violet laser beams and the blue laser beams are incident on the phosphor 110, so that the special light, being the combination of the blue-violet laser beams, the blue laser beams, and the fluorescence from the phosphor 110 excited by the blue laser beams, is applied to the object as illustrated in FIG. 27.

Note that it is preferred to use the phosphor 110 containing two or more types of phosphor components (e.g. YAG-based phosphor, BAM ($BaMgAl_{10}O_{17}$), or the like) which absorb a part of the blue laser beams and emit light of green to yellow colors. In the case where the semiconductor light emitting elements are used as the excitation light sources for the phosphor 110 as described in this example, the high-intensity white light is provided with high light-emission efficiency, the intensity of the white light is controlled easily, and the variations in the color temperature and chromaticity of the white light are small.

(Third Embodiment)

In the third embodiment, instead of the LEDs 20a to 20d of the four colors described in the first embodiment, a broadband light source (e.g. a xenon lamp) and a rotary filter are used to illuminate the object. Instead of the color image sensor 48, a monochrome image sensor is used to image the object. The components other than those are the same as or similar to the components described in the first embodiment.

Figure 28:
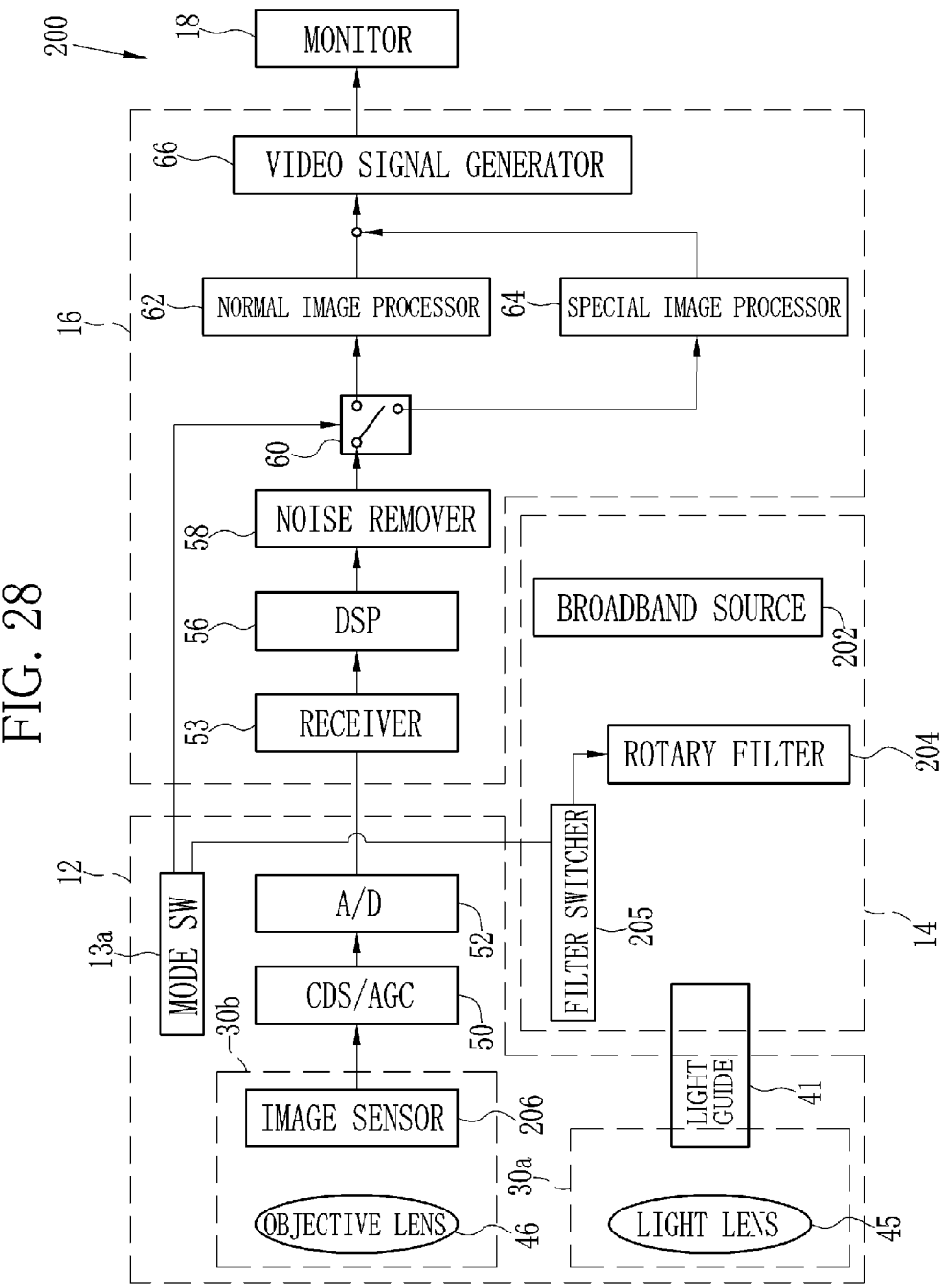
FIG. 28 is a block diagram illustrating functions of an endoscope system according to a third embodiment.

As illustrated in FIG. 28, in an endoscope system 200 of the third embodiment, a broadband light source 202, a rotary filter 204, and a filter switcher 205 are provided instead of the LEDs 20a to 20d in the light source device 14. The imaging optical system 30b is provided with a monochrome image sensor 206 with no color filter, in place of the color image sensor 48.

The broadband light source 202 is composed of a xenon lamp, a white LED, or the like, and emits the white light having the wavelength range from blue to red. The rotary filter 204 comprises a normal filter 208 provided on the inner side and a special filter 209 provided on the outer side (see FIG. 29). The normal filter 208 is used in the normal mode. The special filter 209 is used in the first or second special mode. The filter switcher 205 shifts the rotary filter 204 in the radial direction. When the mode is set to the normal mode by the operation of the mode SW 13a, the normal filter 208 of the rotary filter 204 is inserted into the light path of the white light. When the mode is set to the first or second special mode, the special filter 209 of the rotary filter 204 is inserted into the light path of the white light.

Figure 29:
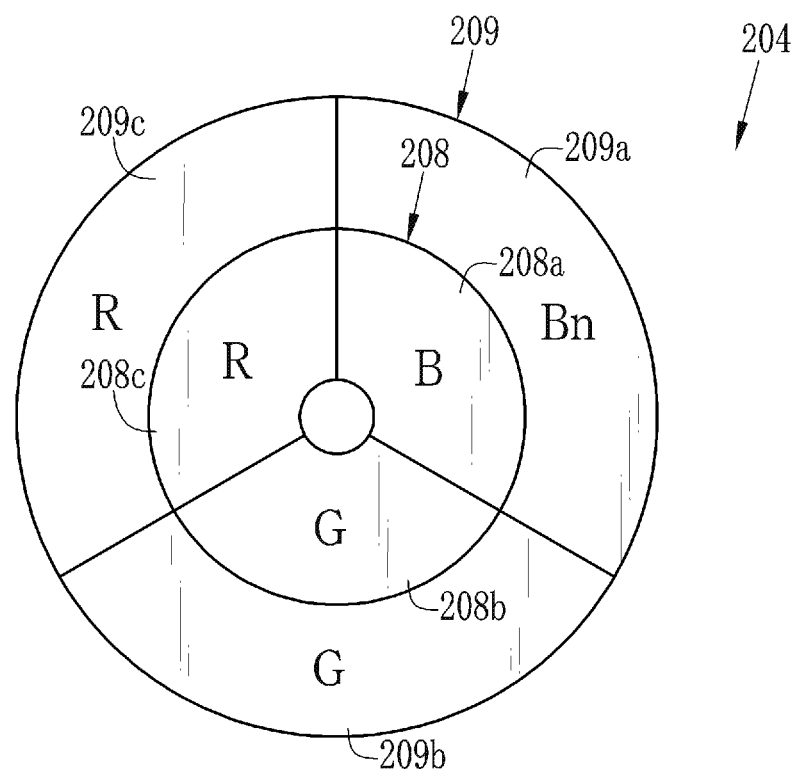
FIG. 29 is a plan view illustrating a rotary filter.

As illustrated in FIG. 29, the normal filter 208 comprises a B filter 208a, a G filter 208b, and an R filter 208c in the circumferential direction. The B filter 208a transmits the blue light of the white light. The G filter 208b transmits the green light of the white light. The R filter 208c transmits the red light of the white light. In the normal mode, the blue light, the green light, and the red light are applied in this order to the object as the rotary filter 204 is rotated.

The special filter 209, which is used in the first or second special mode, comprises a Bn filter 209a, a G filter 209b, and an R filter 209c in the circumferential direction. The Bn filter 209a transmits the blue narrowband light having a specific wavelength range of the white light. The G filter 209b transmits the green light of the white light. The R filter 209c transmits the red light of the white light. In the special mode, the blue narrowband light, the green light, and the red light are applied in this order to the object as the rotary filter 204 is rotated.

In the endoscope system 200, in the normal mode, the monochrome image sensor 206 takes an image of the object every time the blue light, the green light, or the red light is applied to the object. Thereby, the three colors (RGB) of image signals are obtained. The normal image is produced based on the RGB image signals in a manner the same or similar to that in the first embodiment.

In the first or second special mode, the image sensor 206 takes an image of the object every time the blue narrowband light, the green light, or the red light is applied to the object. Thereby, the Bn image signal, the G image signal, and the R image signal are obtained. The first or second special image is produced based on the Bn image signal, the G image signal, and the R image signal. The Bn image signal is used in place of the B image signal to produce the first or second special image. Other than that, the first or second special image is produced in a manner the same as or similar to that of the first embodiment.

(Fourth Embodiment)

In a fourth embodiment, a swallow-type capsule endoscope is used instead of the insertion-type endoscope 12 and the light source device 14, to obtain the RGB image signals necessary for producing the normal image, the first special image, or the second special image.

Figure 30:
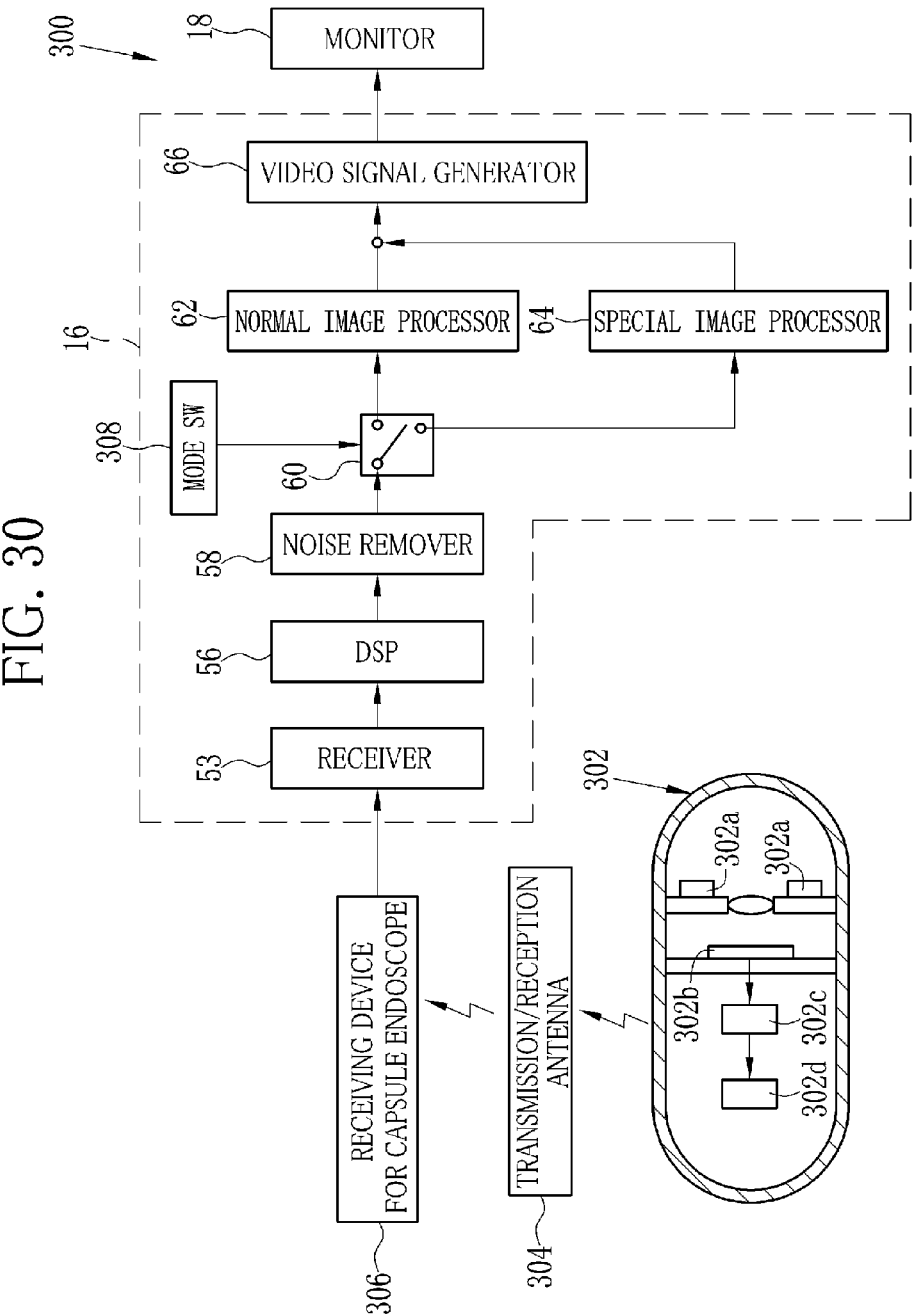
FIG. 30 illustrates functions of a capsule endoscope system according to a fourth embodiment.

As illustrated in FIG. 30, a capsule endoscope system 300 according to the fourth embodiment comprises a capsule endoscope 302, a transmission/reception antenna 304, a receiving device 306 for the capsule endoscope 302, the processor device 16, and the monitor 18. The capsule endoscope 302 comprises an LED 302a, an image sensor 302b, an image processor 302c, and a transmission antenna 302d. Note that the processor device 16 is the same as or similar to the one used in the first embodiment. In the fourth embodiment, a mode switch (SW) 308 is provided to switch among the normal mode, the first special mode, and the second special mode.

Inside the capsule endoscope 302, two or more LEDs 302a that emit white light are provided. Here, it is preferred that the LED 302a is a white light LED which comprises a blue light source and a phosphor which converts wavelengths of light from the blue light source into fluorescence. An LD (laser diode) may be used instead of the LED. The object is illuminated with the white light from the LED 302a.

The image sensor 302b is a color image sensor. The image sensor 302b takes an image of the object illuminated with the white light and outputs the RGB image signals. Here, it is preferred that the image sensor 302b is a CCD (Charge Coupled Device) image sensor or a CMOS (Complementary Metal-Oxide Semiconductor) image sensor. The RGB image signals outputted from the image sensor 302b are subjected, in the image processor 302c, to a process to convert them into signals to be transmitted through the transmission antenna 302d. The RGB image signals, which have passed through the image processor 302c, are transmitted wirelessly from the transmission antenna 302d to the transmission/reception antenna 304.

The transmission/reception antenna 304 is affixed to the subject's body, and receives the RGB image signals from the transmission antenna 302d. The transmission/reception antenna 304 wirelessly transmits the received RGB image signals to the receiving device 306 for the capsule endoscope 302. The receiving device 306 is connected to the receiver 53 of the processor device 16, and transmits the RGB image signals from the transmission/reception antenna 304 to the receiver 53.

Figure 31:
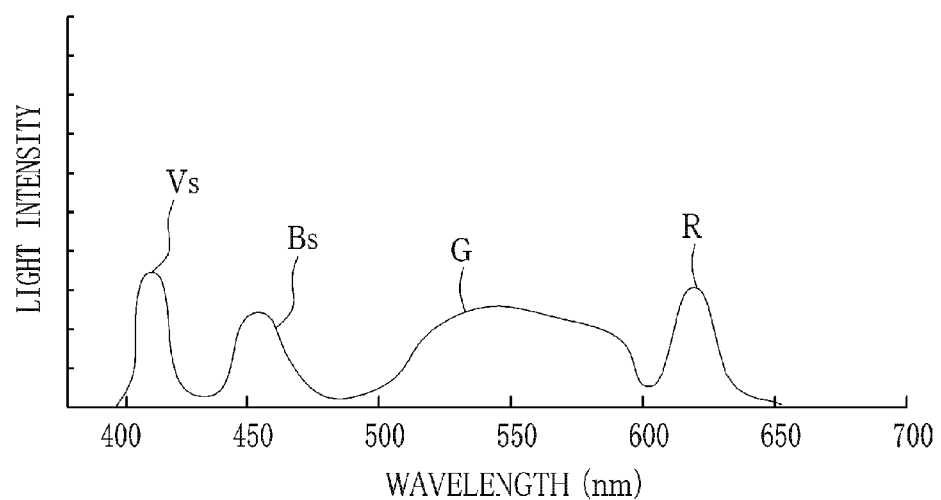
FIG. 31 is a graph illustrating emission spectra of violet light V, blue light B, green light G, and red light R which are different from those of FIG. 3.

Note that, in the above embodiments, the four colors of light with the emission spectra illustrated in FIG. 3 are used by way of example. The emission spectra are not limited to this example. For example, as illustrated in FIG. 31, the green light G and the red light R may have the same spectra as those illustrated in FIG. 3. The violet light Vs may have the center wavelength 410 to 420 nm in a wavelength range slightly shifted to a longer wavelength side than that of the violet light V in FIG. 3. The blue light Bs may have the center wavelength 445 to 460 nm in a wavelength range slightly shifted to a shorter wavelength side than that of the blue light B in FIG. 3.

Figure 32:
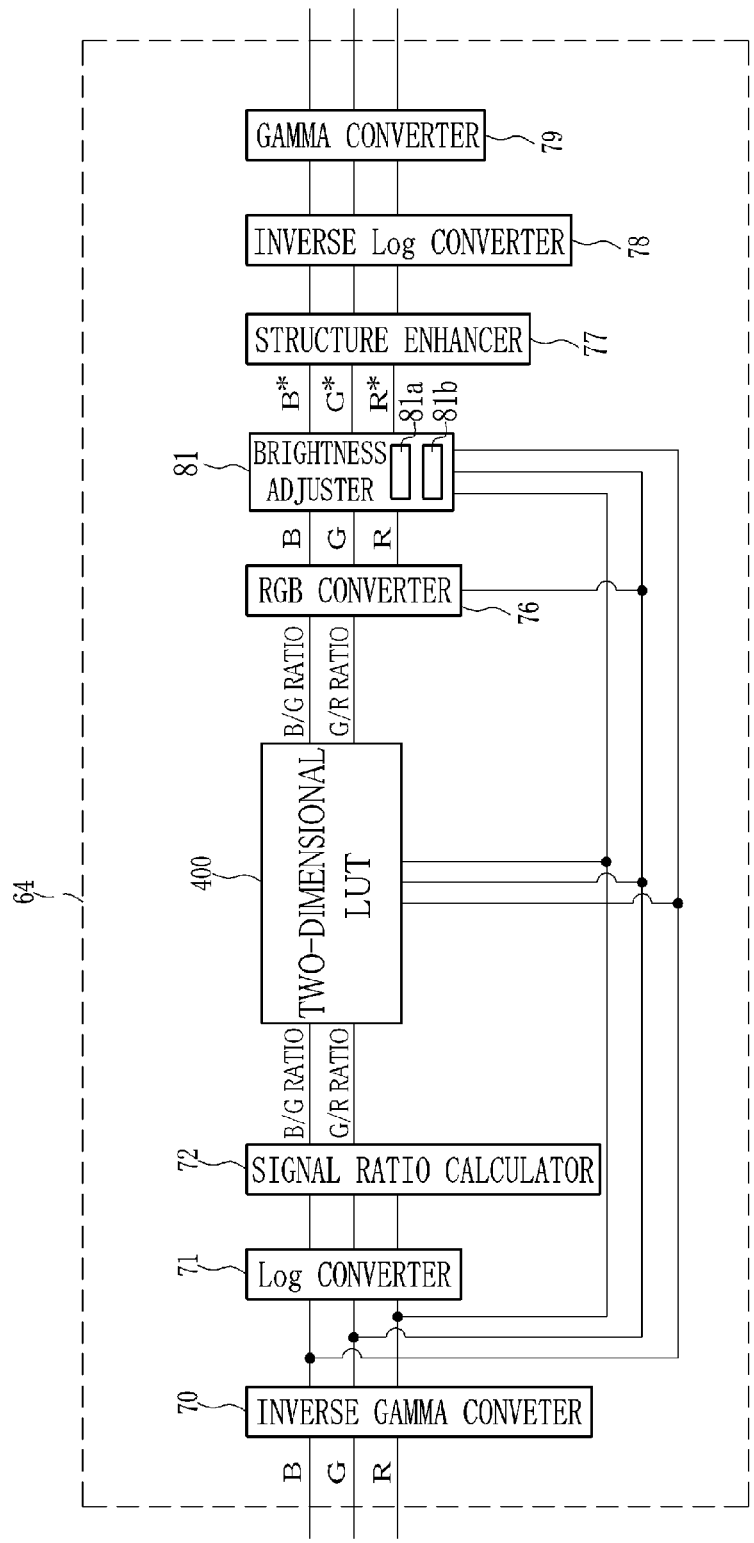
FIG. 32 is a block diagram illustrating functions of the special image processor in a case where a two-dimensional LUT is used.

Note that, in the above embodiments, the B/G ratio and the G/R ratio are converted into the radial coordinate r and the angular coordinate θ through the polar coordinate conversion. The first or second process for expanding or compressing the angle is performed based on the radial coordinate r and the angular coordinate θ. Thereafter, the radial coordinate r and the angular coordinate θ are converted back into the B/G ratio and the G/R ratio. Alternatively, as illustrated in FIG. 32, a two-dimensional LUT 400 may be used to directly convert the B/G and G/R ratios into the processed B/G and G/R ratios, which have been subjected to the first or second process, without the polar coordinate conversion.

Note that the two-dimensional LUT 400 stores the B/G and G/R ratios in association with the processed B/G and G/R ratios, which have been subjected to the first or second process based on the B/G and G/R ratios. The first RGB image signals outputted from the inverse gamma converter 70 are inputted to the two-dimensional LUT 400. Alternatively, the first RGB image signals may be inputted to the RGB converter 76, in a manner similar to the above embodiments.

Note that, in the above embodiments, the angles θ1 and θ2 of the coordinates in the feature space are changed by the expansion process and the compression process so as to make the difference in color apparent between the portion infected with the *H. pylori* and the portion in which the eradication of the *H. pylori* has been successful or between the portion infected with the *H. pylori* and the portion uninfected with the *H. pylori*, by way of example. The methods described in the above embodiments are applicable to any comparison of colors between two different portions of an object of interest.

Figure 33:
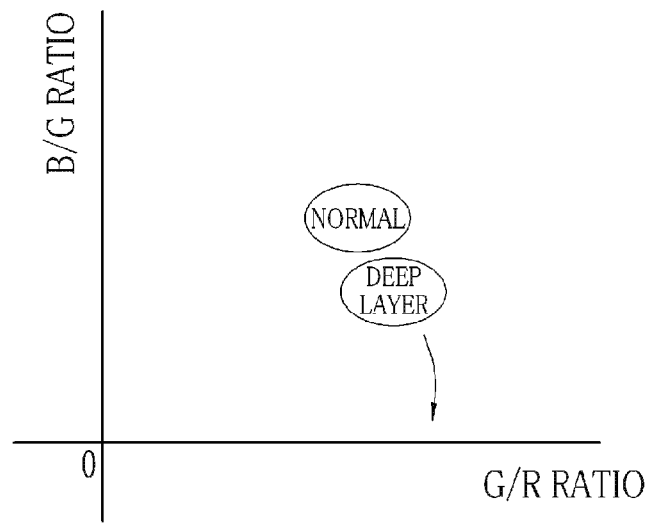
FIG. 33 is an explanatory view illustrating areas in which normal mucosa and deep-layer blood vessels are located in the feature space (vertical axis: B/G ratio, horizontal axis: G/R ratio)

For example, in the case of the atrophic gastritis, it is known that the color of a portion (tissue) with deep blood vessels changes, due to the color of the deep blood vessels seen through the tissue, as the thickness of the tissue decreases with the progression of the atrophy of the stomach. This phenomenon is expressed in the feature space (the vertical axis: B/G ratio, the horizontal axis: G/R ratio) illustrated in FIG. 33. In the absence of the atrophic gastritis, the coordinates in a fourth observation area (denoted as "deep layer" in FIG. 33), in which the deep blood vessels are mostly distributed, are in proximity to the coordinates in a fifth observation area (denoted as "normal" in FIG. 33), in which the normal mucosa is mostly distributed, in the feature space. The coordinates corresponding to the fourth observation area shift in the clockwise direction and move away from the coordinates corresponding to the fifth observation area as the atrophy of the stomach progresses.

In an advanced stage of the atrophy of the stomach, the difference between the fourth observation area and the fifth observation area is significant, so that a change in color of the portion with the deep blood vessels seen through the thin tissue is noticeable. However, in the case where the atrophy of the stomach is in its early stage and the difference between the fourth observation area and the fifth observation area is small, it is often difficult to notice the change in color of the portion with the deep blood vessels. In the case where the atrophy of the stomach is in its early stage, a third process, which is composed of the expansion process and the compression process, is performed to increase the difference between the fourth observation area and the fifth observation area. Thereby, the change in color of the portion with the deep blood vessels becomes easily noticeable.

Figure 34:
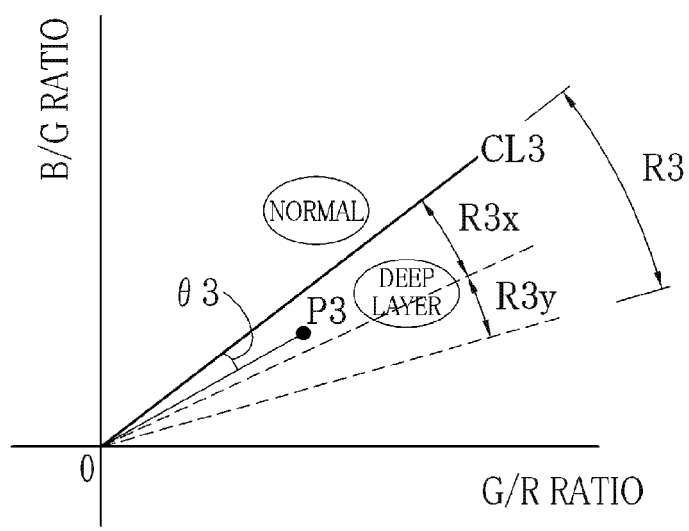
FIG. 34 is an explanatory view illustrating a third process.

The angle expansion/compression unit 74 performs the third process in the signal ratio space. In the third process (for the signal ratio space), as illustrated in FIG. 34, a region including the fourth observation area and the fifth observation area is set as an angle changing region R3 in the feature space (the vertical axis: B/G ratio, the horizontal axis: G/R ratio). The deep blood vessels are mostly distributed in the fourth observation area (denoted as "deep layer" in FIG. 34). The normal mucosa is mostly distributed in the fifth observation area (denoted as "normal" in FIG. 34). Then the angle θ3 of coordinates (point) P3 in the angle changing region R3 is changed while the angle of the coordinates outside the angle changing region R3 is not changed. In the third process (for the signal ratio space), the radial coordinate r of the coordinates in the angle changing region R3 is not changed.

In the angle changing region R3, a third center line CL3 is provided between the fourth observation area and the fifth observation area. The coordinates P3 within the angle changing region R3 are defined by the angle "θ3" from the third center line CL3. The angle θ3 which is located in the clockwise direction from the third center line CL3 is defined as a positive angle.

In the third process (for the signal ratio space), the expansion process is performed on the angle θ3 in a specific angle changing region R3x, which extends from (or contains) the third center line CL3 and within the angle changing region R3. In the expansion process, the angle θ3 is changed at an angle change rate W3x that is greater than "1". In an angle changing region R3y outside the angle changing region R3x, the compression process is performed. In the compression process, an angle is changed at an angle change rate W3y that is less than "1". The coordinates in the angle changing region R3 are moved within a region, which extends +90° from the third center line CL3, by the expansion process and the compression process.

The above-described expansion process and the compression process increase the difference between the fourth observation area ("deep layer") and the fifth observation area ("normal"). In a third special image, in which the difference between the fourth observation area and the fifth observation area has been increased, the change in color of the portion with the deep blood vessels is positively identified even at the early stage of the atrophy of the stomach. The region extending +90° from the third center line CL3 is a specific color region in which the difference in color (referred to as the "color difference" in this paragraph) between the portion with the normal mucosa and the portion with the deep blood vessels is emphasized. In a region beyond +90° from the third center line CL3, being a region outside the specific color region, the color difference is not emphasized by changing the angle. In the third process (for the signal ratio space), the compression process is performed in addition to the expansion process so that the angle after the expansion process or the compression process is within the region extending +90° from the third center line CL3. As a result, in the third special image, the color difference in the specific color region is emphasized while the color difference in the region other than the specific color region is not emphasized.

Note that the present invention is applicable to various types of medical image processing devices in addition to the endoscope systems described in the first to third embodiments and the processor device incorporated in the capsule endoscope system described in the fourth embodiment.

Various changes and modifications are possible in the present invention and may be understood to be within the present invention.

What is claimed is:

1. A medical image processing device comprising:
a processing circuitry configured for:
performing an input process of a first color image signal;
obtaining two or more pieces of color information from the first color image signal; and
performing an expansion process for changing an angle between a center line and a line that passes through coordinates within a specific angle changing region Rnx containing the center line at an angle change rate Wnx and a compression process for changing an angle between the center line and a line that passes through coordinates within an angle changing region Rny beyond the angle changing region Rnx at an angle change rate Wny in a feature space being a two-dimensional space formed by the two or more pieces of color information, the angle change rate Wny being less than the angle change rate Wnx.

2. The medical image processing device according to claim 1, wherein first and second observation areas to be observed are distributed in the feature space, and a distance between the first observation area and the second observation area is D1, and
the center line is a first center line provided between the first observation area and the second observation area, and
the angle changing region Rnx is an angle changing region R1x containing the first center line, and the angle changing region Rny is an angle changing region R1y beyond the angle changing region R1x, and
the angle change rate Wnx is an angle change rate W1x greater than 1, and the angle change rate Wny is an angle change rate W1y less than 1.

3. The medical image processing device according to claim 2, wherein the first observation area, the second observation area, and a third observation area are distributed in the feature space, and a distance D2 between the first observation area and the third observation area is greater than the distance D1, and
the center line is a second center line provided between the first observation area and the third observation area, and
the angle changing region Rnx is an angle changing region R2x containing the second center line, and the angle changing region Rny is an angle changing region R2y beyond the angle changing region R2x, and
the angle change rate Wnx is an angle change rate W2x greater than 1, and the angle change rate Wny is an angle change rate W2y less than 1.

4. The medical image processing device according to claim 3, wherein the angle after the expansion process or the compression process is within a region extending between ±90° from the first or second center line.

5. The medical image processing device according to claim 1, wherein fourth and fifth observation areas to be observed are distributed in the feature space, and
the center line is a third center line provided between the fourth observation area and the fifth observation area, the angle changing region Rnx is a specific angle changing region R3x located on a fourth observation area side from the third center line, and the angle changing region Rny is an angle changing region R3y beyond the angle changing region R3x, and
the angle change rate Wnx is an angle change rate W3x greater than 1, and the angle change rate Wny is an angle change rate W3y less than 1.

6. The medical image processing device according to claim 1, wherein the first color image signal is composed of image signals of three colors, and the two or more pieces of color information is composed of a first signal ratio between the image signals of the two colors of out of the image signals of the three colors and a second signal ratio between the image signals of the two colors out of the image signals of the three colors, and one of the colors of the image signals of the second signal ratio differs from the colors of the image signals of the first signal ratio, and the feature space is a signal ratio space formed by the first and second signal ratios.

7. The medical image processing device according to claim 6, wherein the first signal ratio correlates with a blood vessel depth and the second signal ratio correlates with a blood volume.

8. The medical image processing device according to claim 7, wherein the first signal ratio is a B/G ratio and the second signal ratio is a G/R ratio.

9. The medical image processing device according to claim 1, wherein the feature space is any one of Cb-Cr space formed by chrominance signals Cr and Cb, being the two or more pieces of color information, and ab space formed by color components a* and b*, being the two or more pieces of color information, in a CIE Lab space.

10. The medical image processing device according to claim 1, further comprising:
a color image signal converter for converting the two or more pieces of color information, which have been subjected to the processes in the processor, into a second color image signal, and
a brightness adjuster for adjusting a pixel value of the second color image signal based on first brightness information obtained from the first color image signal and second brightness information obtained from the second color image signal.

11. A method for operating a medical image processing device comprising the steps of:
performing an input process of a first color image signal with an input processing unit;
obtaining two or more pieces of color information from the first color image signal with a color information obtaining section; and
performing an expansion process for changing an angle between a center line and a line that passes through coordinates within a specific angle changing region Rnx containing the centerline at an angle change rate Wnx and a compression process for changing an angle between the center line and a line that passes through coordinates within an angle changing region Rny beyond the angle changing region Rnx at an angle change rate Wny in a feature space with a processor, the feature space being a two-dimensioal space formed by the two or more pieces of color information, the angle change rate Wny being less than the angle change rate Wnx.

* * * * *